United States Patent
Welch et al.

[11] Patent Number: 6,140,647
[45] Date of Patent: Oct. 31, 2000

[54] GASOLINE RFG ANALYSIS BY A SPECTROMETER

[75] Inventors: William T Welch, Ashland, Ky.; Roy R. Bledsoe, Huntington, W. Va.; Brian K. Wilt, Ashland, Ky.; Michael B. Sumner, Huntington, W. Va.

[73] Assignee: Marathon Ashland Petroleum

[21] Appl. No.: 08/994,787

[22] Filed: Dec. 19, 1997

[51] Int. Cl.[7] .................................................. G01J 3/42
[52] U.S. Cl. .............................. 250/339.12; 250/339.09
[58] Field of Search ..................... 250/339.12, 339.08, 250/339.09

[56] References Cited

U.S. PATENT DOCUMENTS

| | | | |
|---|---|---|---|
| 5,223,714 | 6/1993 | Maggard | 250/339.12 |
| 5,349,188 | 9/1994 | Maggard | 250/339.12 |
| 5,349,189 | 9/1994 | Maggard | 250/339.12 |
| 5,360,972 | 11/1994 | DiFoggio et al. | 250/339.12 |
| 5,412,581 | 5/1995 | Tackett | 250/339.01 |
| 5,475,612 | 12/1995 | Espinosa et al. | 250/339.07 |
| 5,596,196 | 1/1997 | Cooper et al. | 250/339.12 |
| 5,712,481 | 1/1998 | Welch et al. | 250/339.12 |

*Primary Examiner*—Constantine Hannaher
*Attorney, Agent, or Firm*—Richard C. Willson, Jr.; Richard D. Stone; A. J. Adamcik

[57] ABSTRACT

Reformulated gasoline (RFG) testing recently required by EPA involves measuring sulfur, olefin, aromatic contents, Reid Vapor Pressure (RVP), and benzene, distillation properties, plus total air pollutants (TAPs), volatile organic carbon (VOC), and nitrogen oxides (NOx). Measuring driveability, although not required, is desirable. All of these tests can be conducted by spectrometer, preferably in the IR range, more preferably in the NIR range, and most preferably by a single instrument operating at high-correlation wavelengths. Importantly, VOC, TAP, NOx, and RVP may be correlated to IR absorbance at certain bands. Statistical methods including PLS, MLR, PCR, and neural networks can be used and derivatives of first, particularly second, or other orders can be used. Results can be displayed on a single screen.

46 Claims, 13 Drawing Sheets

GASOLINE RFG ANALYSIS BY A SPECTROMETER

BACKGROUND OF THE INVENTION

I. Field of the Invention

The present invention relates to techniques of analysis, particularly of hydrocarbons and substituted hydrocarbon mixtures generally classified in Class 250.

II. Description of the Prior Art

There are a number of ASTM (American Society for Testing Materials) and other standard methods for the analysis of physical properties of hydrocarbons such as ASTM D-86 distillation temperatures at various percentages distilled; ASTM D-1298 test for API gravity; Gas chromatography —Mass spectrometry (GC Mass Spec) for determination of weight percent aromatics; and ASTM D-2622 for sulfur.

Conventionally, these tests are conducted by enough different test apparatus to fill a small laboratory and are time-consuming and relatively expensive, particularly when applied to the hundreds of samples per day which may be required to be analyzed in a typical refinery. This situation will be made much more acute with the new reformulated fuel requirements for the prediction of total air pollutants (TAPs) exhaust benzene, volatile organic carbon (VOC), nitrogen oxides (NOx), Reid vapor pressure (RVP), and driveability index. Reformulated gasoline is defined in the Federal Register (59CFR32): ". . . any gasoline whose formulation has been certified under §80.40, which meets each of the standards and requirements prescribed under §80.41, and which contains less than the maximum concentration of the marker specified in §80.82 that is allowed for reformulation under §80.82." Effective Jan. 1, 1995, U.S. goverment regulations require these to be calculated by a "simple" model.

Simple Model

Exhaust Benzene=1.884+0.949(Vol % Benzene)+0.113 (Vol % Aromatics–Vol % Benzene)

Total Toxics=Exhaust Benzene+Refueling Benzene+ Evaporative Benzene+Running Loss Benzene+ Butadiene+Formaldehyde+Acetaldehyde+POM

```
   Refueling Benzene = Vol % Benzene (Refueling VOC) (10)
                       [1.3972 - 0.591
                       (MTBE Wt % Oxygen/2) - 0.081507 (RVP)]
 Evaporative Benzene = Vol % Benzene (10) (Evaporative VOC)
                       {0.679 [1.4448 - 0.0684 (MTBE Wt %
                       Oxygen/2 - 0.080274 (RVP)]} + 0.0321
                       [1.3758 - 0.579
                       (MTBE Wt % Oxygen(2) - 0.080274 (RVP)]
Running Loss Benzene = Vol % Benzene (Running loss VOC) (10)
                       [1.4448 - 0.684 (MTBE Wt %
                       Oxygen/2) - 0.080274 (RVP)
           Butadiene = 0.00556 (Exhaust VOC) 1000
        Formaldehyde = 0.01256 (Exhaust VOC) 1000 [1 + (0.421/2.7)
                       (MTBE Wt % Oxygen + TAME Wt %
                       Oxygen + (0.358/3.55 (EtOH Wt %
                       Oxygen) + 0.137/2.7) (ETBE Wt %
                       Oxygen + ETAE Wt % Oxygen)]
        Acetaldehyde = 0.00891 (Exhaust VOC) 1000 [1 + (0.078/2.7)
                       (MTBE Wt % Oxygen + TAME Wt %
                       Oxygen) + (0.865/3.55) (EtOH Wt %
                       Oxygen) + 0.867/2.7)
                       (ETBE Wt % Oxygen + ETAE Wt %
                       Oxygen)]
                 POM = 3.15 (Exhaust VOC)
```

Exhaust VOC=0.444[=0127/2.7)(sum of Wt % Oxygen from MTBE, ETBE, TAME, ETAE)

Refueling VOC=0.04[0.1667(RVP)–0.45]

Evaporative VOC=0.813–0.2393(RVP)+0.21239(RVP) (RVP)

Running Loss VOC=0.2963–0.1306(RVP)+0.016255 (RVP)(RVP)

At some time in the future, government regulators may require a more sophisticated "complex" model for prediction of these environmental parameters of fuels. The complex model contains more detailed calculations and two additional parameters: Total NOx (Nitrogen Oxides) and Total VOC (Volatile Organic Carbon). Since individual refineries will have to certify the VOC, NOx, TAP, benzene, and RVP of their fuels on a daily or more frequent basis, the number of tests and their complexity will pose a daunting problem to the refinery industry.

Chemometric models obtained may be used with a laboratory spectrophotometer to determine component concentrations or from physical properties of test samples. Alternatively, an on-line spectrometer installed on or "at" a gasoline stream may be used to predict real time concentrations and physical properties.

A significant amount of work has been done on use of spectroscopy to determine fuel properties.

U.S. Pat. No. 4,963,745 to Maggard teaches octane measured by NIR methyne band, etc.; U.S. Pat. No. 5,223,714 to Maggard teaches a prediction of octane, etc., using linear addition with or without NIR; U.S. Pat. No. 5,349,188 to Maggard teaches the determination of octane by secondary wavelengths in the NIR; U.S. Pat. No. 5,349,189 to Maggard teaches PIANO determination by NIR; U.S. Pat. No. 5,243, 546 to Maggard teaches transfer of calibration equations in the NIR; U.S. Pat. No. 5,145,785 to Maggard et al. teaches aromatic content of diesel measured by NIR; U.S. Pat. No. 5,370,790 to Maggard et al. teaches aromatic content of diesel measured by NIR and relates to the apparatus; U.S. Pat. No. 5,348,645 to Maggard et al. teaches the measurement of sulfur content of diesel fuels by NIR; U.S. Pat. No. 5,362,965 to Maggard teaches the direct relationship between the second derivative of the NIR data and concentration of the component.

*Experience Leads to Accurate Design of NIR Gasoline Analysis Systems*, Welch, Bain, Maggard, and May, Oil & Gas Journal, Jun. 27, 1994, pp 48–56, determines research octane, motor octane, road octane, aromatics, olefins, RVP, benzene, oxygen content, and distillation points during gasoline blending.

U.S. Pat. No. 5,596,196, John B. Cooper et al., teaches Oxygenate Analysis and Control by Raman Spectroscopy.

Reformulated gasoline (RFG) testing thus involves measuring sulfur, olefin, aromatic contents, Reid Vapor Pressure (RVP), and benzene, distillation properties, plus total air pollutants (TAPs), exhaust benzene, volatile organic carbon (VOC), and nitrogen oxides (NOx). Measuring driveability, although not required, is desirable.

All of these tests can be conducted by using a spectrometer, preferably in the IR range, more preferably in the NIR range, and most preferably by a single instrument operating at high-correlation wavelengths. Measured Raman intensities may also be used. Importantly, VOC, TAP, exhaust benzene, NOx, and RVP may be correlated to IR absorbance at certain bands. Statistical methods including partial least squares analysis (PLS), multiple linear regression analysis (MLR), principal component regression analysis (PCR), and neural networks can be used and derivatives of first, particularly second, or other orders can be used.

Level 3 or 4 SIMCA may be utilized. As used hereinafter, the term "SIMCA" is employed as commonly understood to refer to soft independent modeling of class analogy. Results can be displayed on a single screen. By predicting simple or complex EPA model values measured by the present invention (NIR, Mid-IR, or Raman embodiments) and comparing the results with results obtained by inserting laboratory values measured by conventional methods into the EPA model, the present invention remains accurate while providing the advantage of labor saving discussed above.

SUMMARY OF THE INVENTION

Accordingly, the present invention provides a process for the determination and/or control of EPA parameters of a gasoline blend (e.g., total toxics, exhaust benzene, VOC's and/or NOx). The present invention comprises in combination, measuring the absorbance or intensity of a liquid hydrocarbon or a component thereof in at least one band in the electromagnetic spectrum, transforming said absorbance by a mathematical transformation comprising multivariate regression analysis, substituting said absorbance or intensity into an equation which predicts one or more EPA parameters or one component thereof of said fuels, and controlling blending of components which affect the TAP of said blend in response to said prediction.

In another embodiment, the present invention provides a method for determining predicted emissions from evaporation and combustion of fuels in an internal combustion engine comprising taking multiple fuel samples and spectrally analyzing each of said samples for at least one of benzene, total aromatics, RVP, wt % oxygen, required distillation points, olefins and sulfur to determine the concentration of said analyzed component using said spectrally determined concentration in a mathematical model for determining total emissions from said determined values and predicting emissions for each fuel sample correlating the spectral data for each fuel sample with said predicted emissions; and predicting emissions from additional fuel samples based on said correlations.

Figure 1:
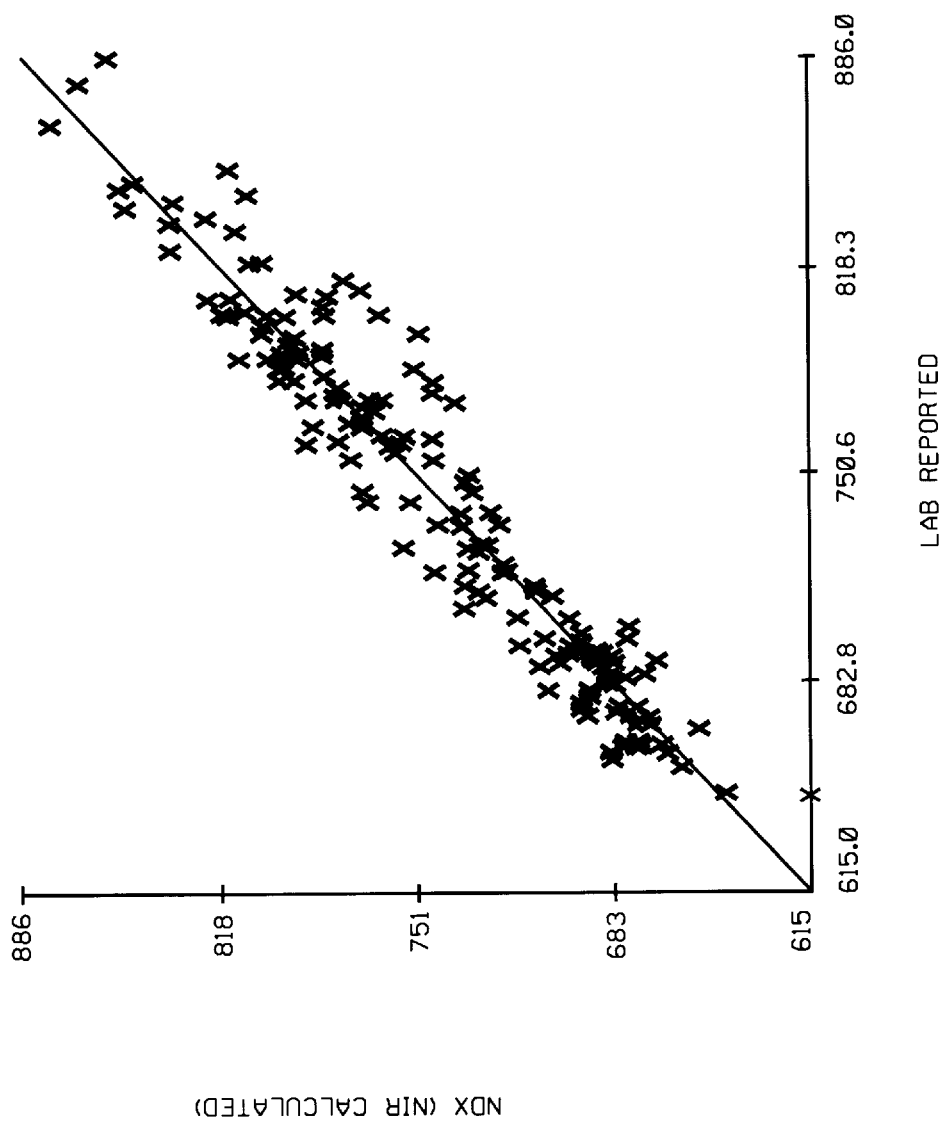
FIG. 1 is a correlation plot of Phase I complex model NOx for winter gasoline, with NIR-predicted NOx plotted against the corresponding Phase I NOx values obtained by inserting the conventional "lab reported" oxygenates, sulfur, RVP, PIANO results for aromatics, olefins and benzene, and distillation by ASTM D-3710 into the EPA complex formula. PIANO is a conventional method which produces results comparable with that of GC-Mass spectrometry for aromatics, fluorescent indicator analysis (FIA) for olefins, and ASDTM D-3606 for benzene by gas chromatography. ASTM D-3710 is a conventional method which produces results comparable with those of ASTM D-86. Oxygenates are determined by ASTM-D5599 and sulfur by ASTM D2622.
Figure 2:
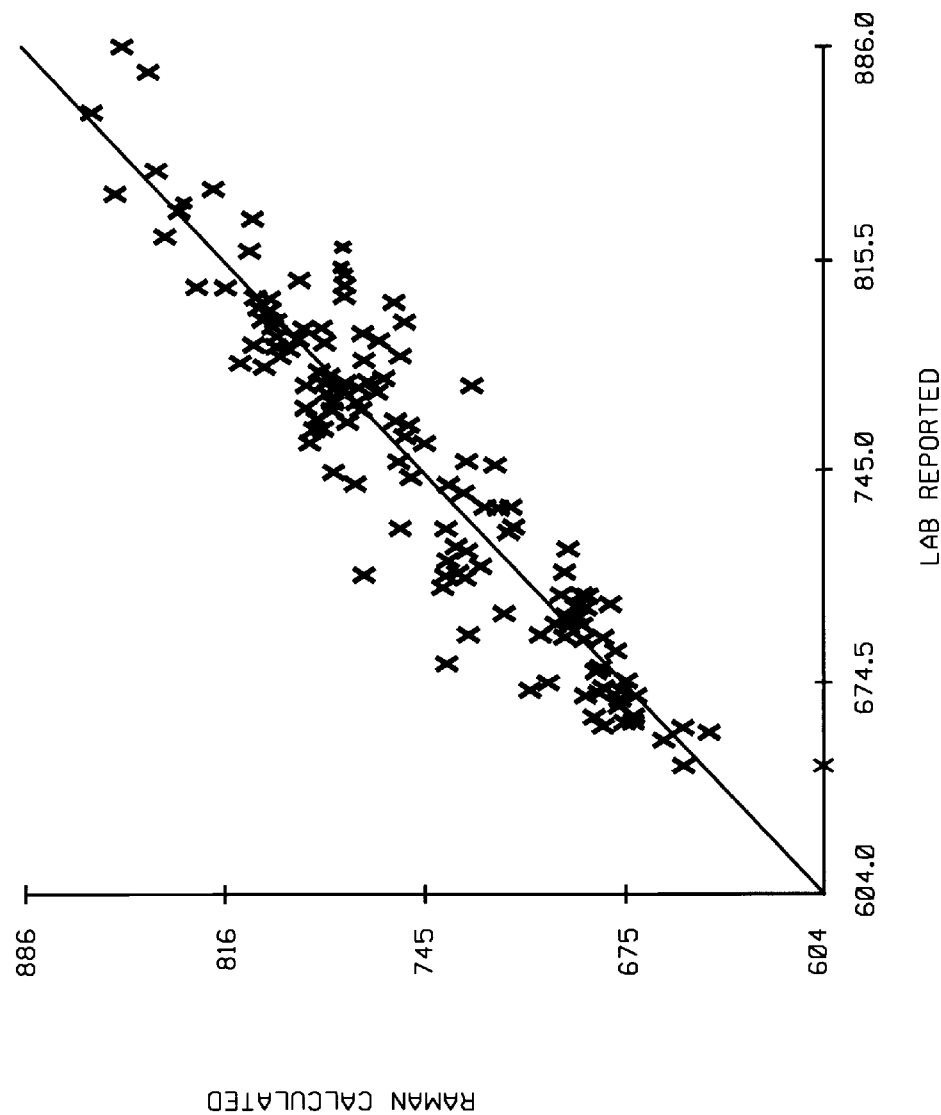
FIG. 2 is a similar plot against the same conventional determinations but comparing the Raman embodiment of this invention.
Figure 3:
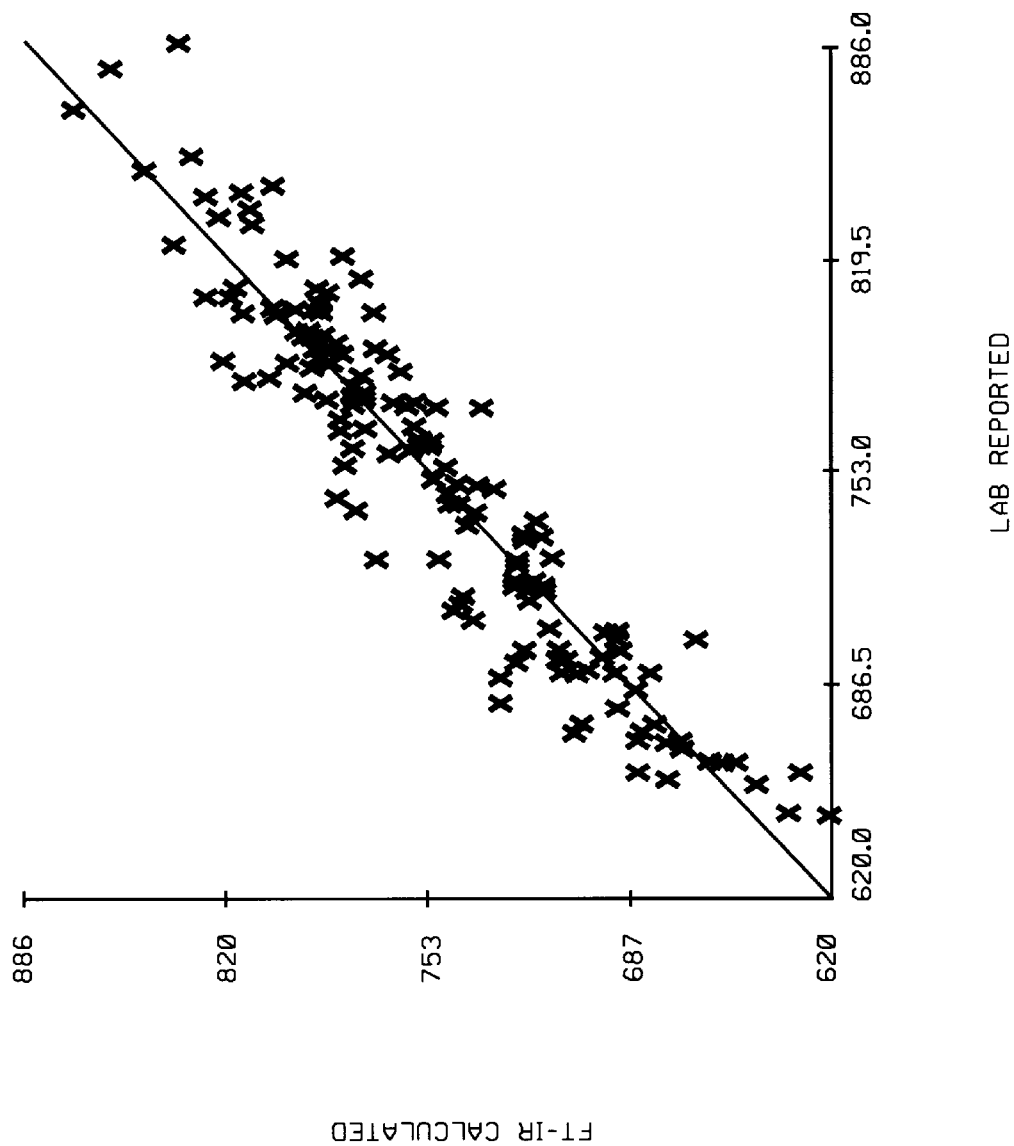
FIG. 3 is a similar plot against conventional determinations but comparing the FT-IR predicted value according to the present invention.
Figure 4:
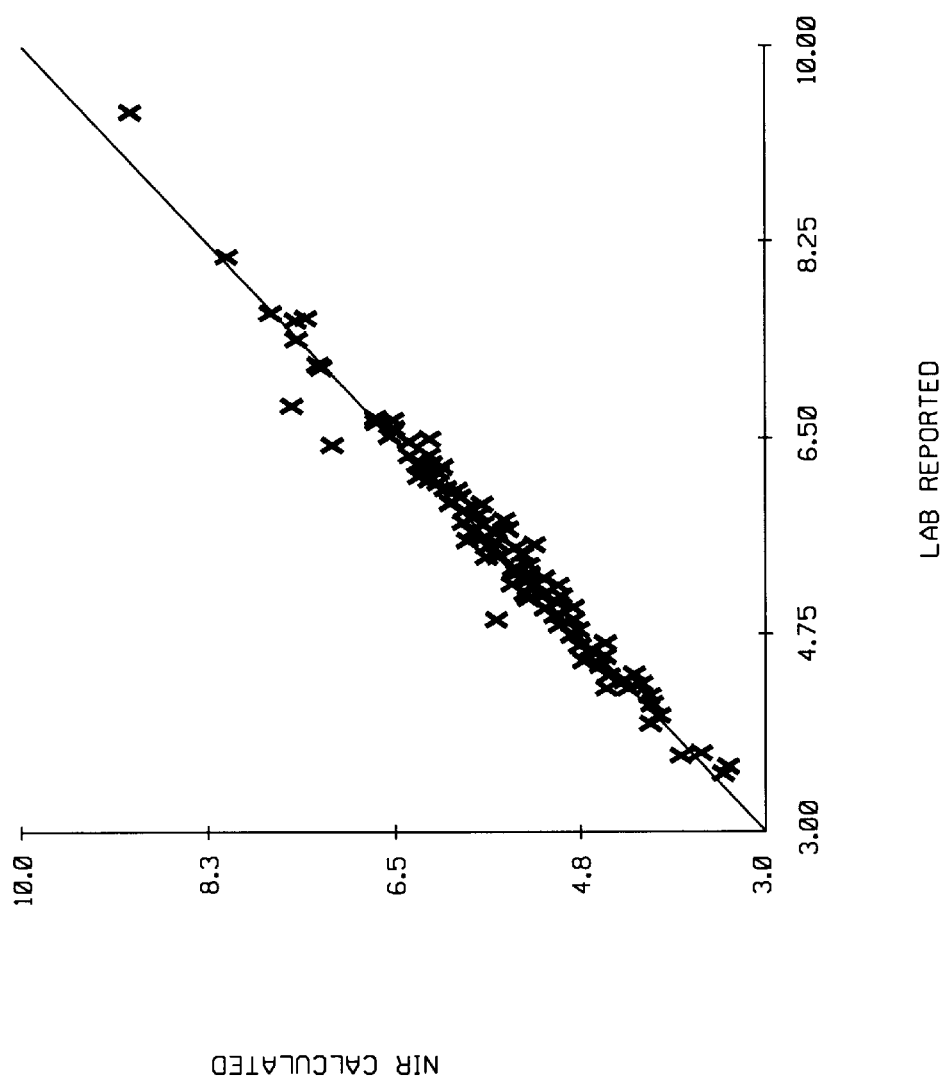
FIGS. 4, 5 and 6 are correlation plots similar to FIGS. 1, 2 and 3, respectively, except that they are for exhaust benzene rather than Phase I NOx
Figure 5:
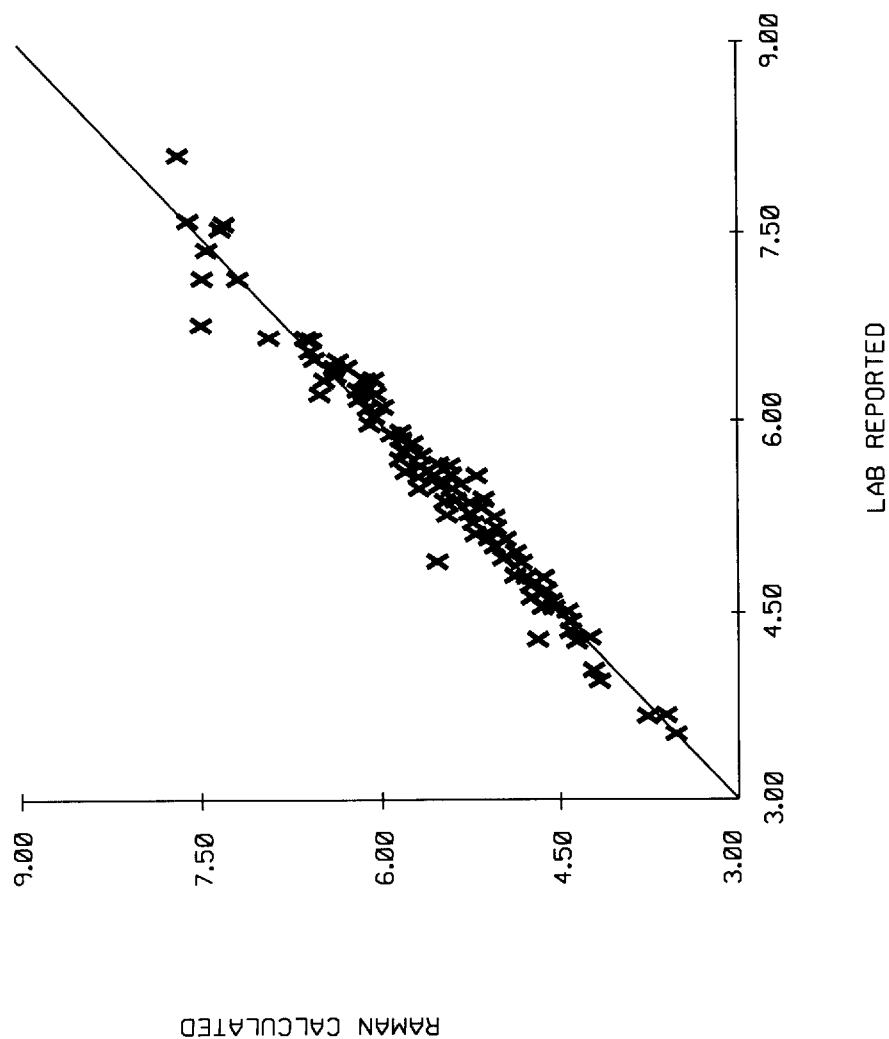
Figure 6:
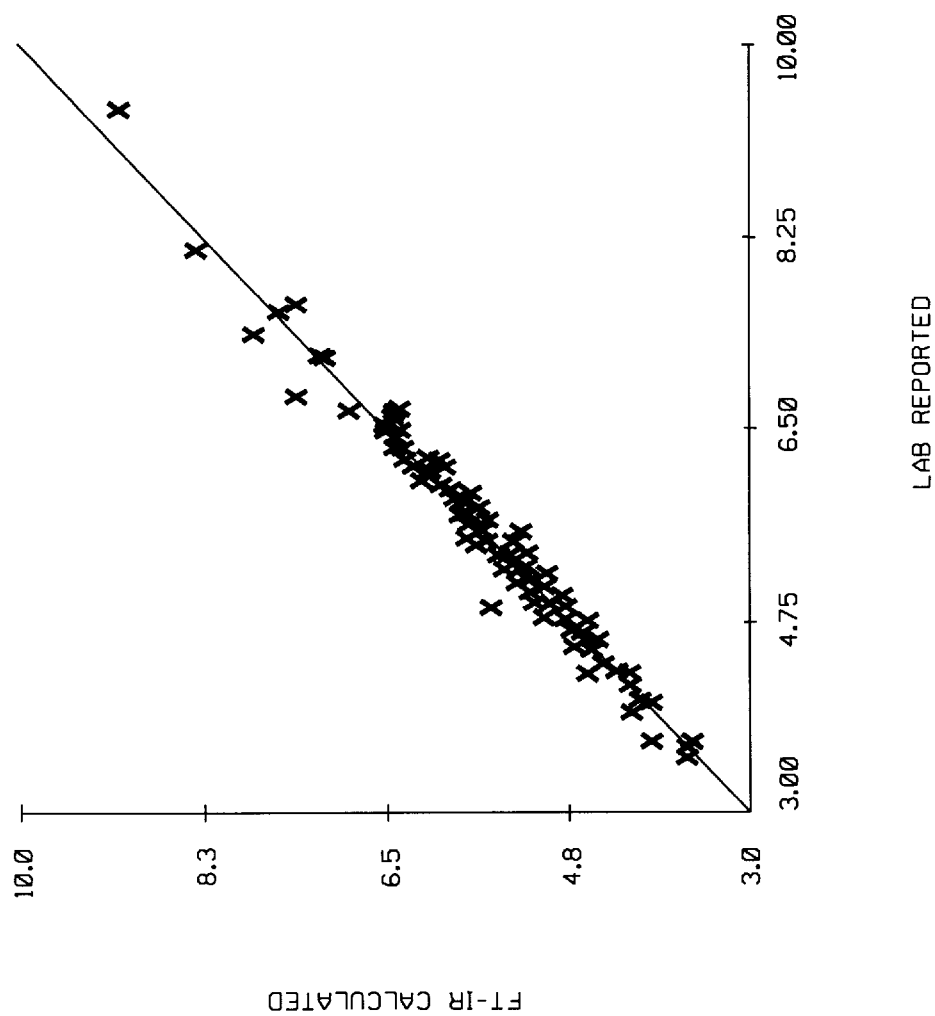
Figure 7:
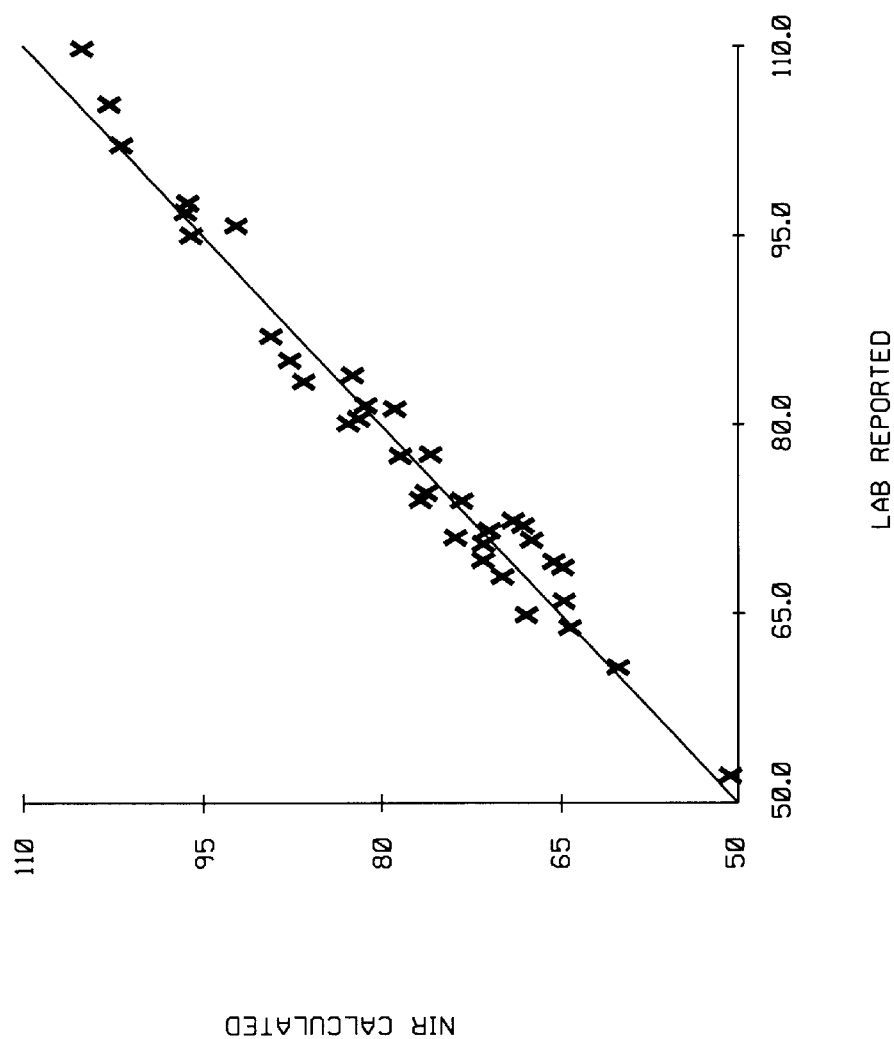
FIGS. 7, 8 and 9 are similar to FIGS. 1, 2 and 3 except that they are for summer gasoline and for Phase II total toxics.
Figure 8:
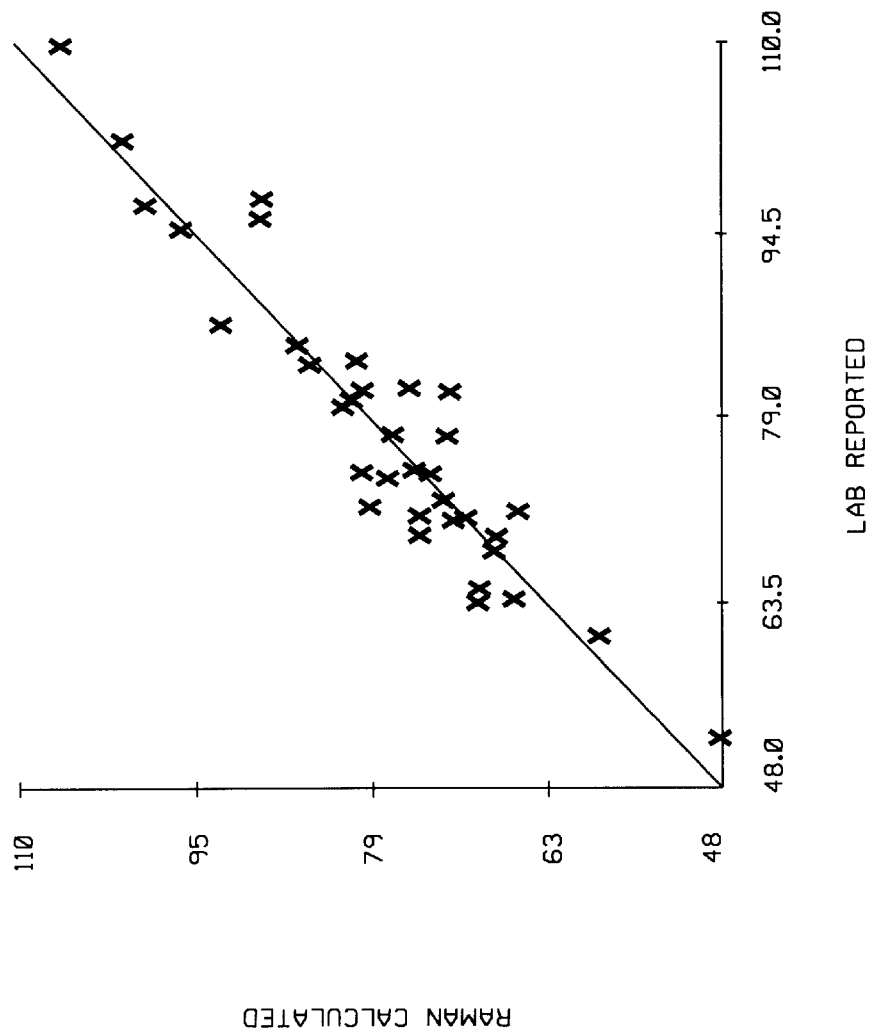
Figure 9:
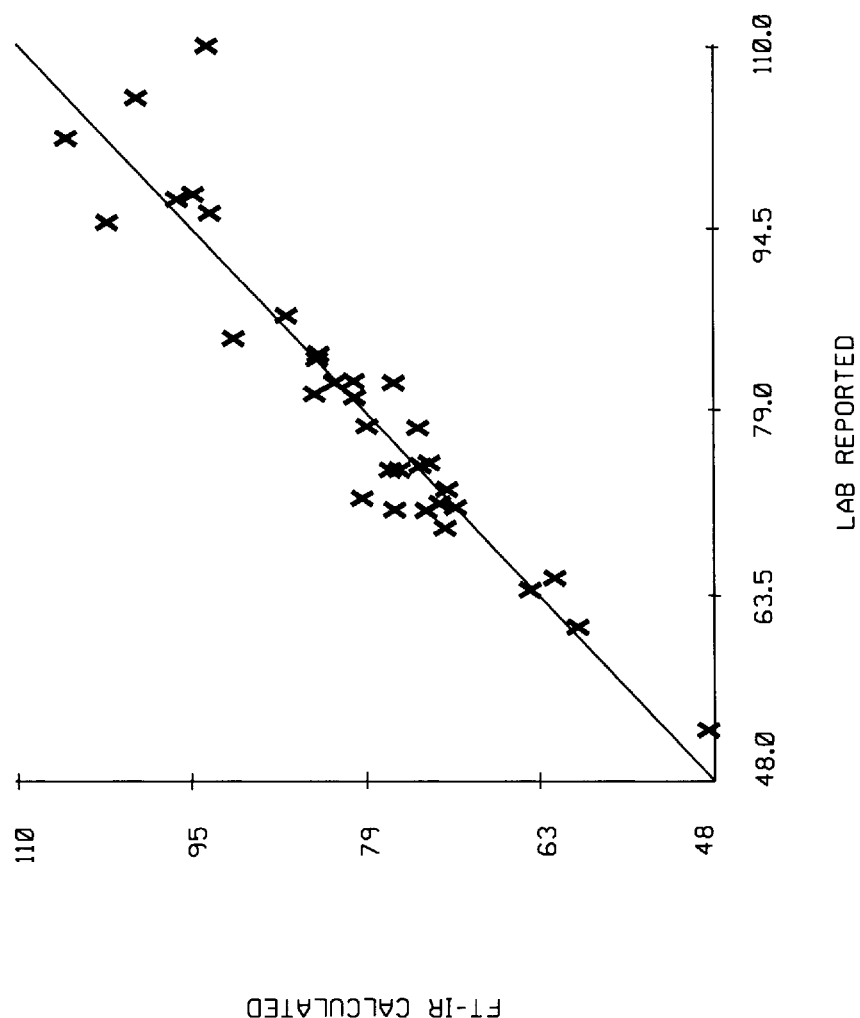
Figure 10:
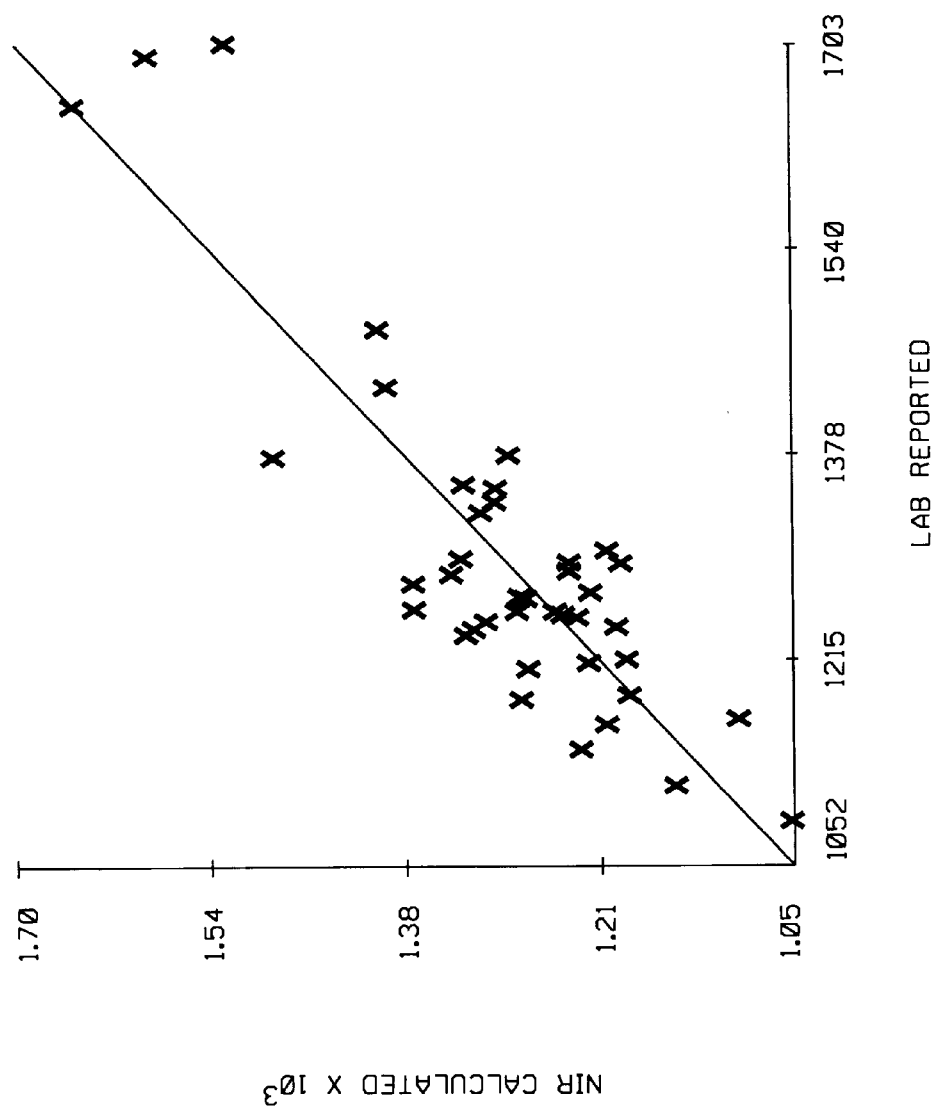
FIGS. 10, 11 and 12 are similar to FIGS. 1, 2 and 3 except that they are correlation plots for summer gasoline and for Phase II total VOC.
Figure 11:
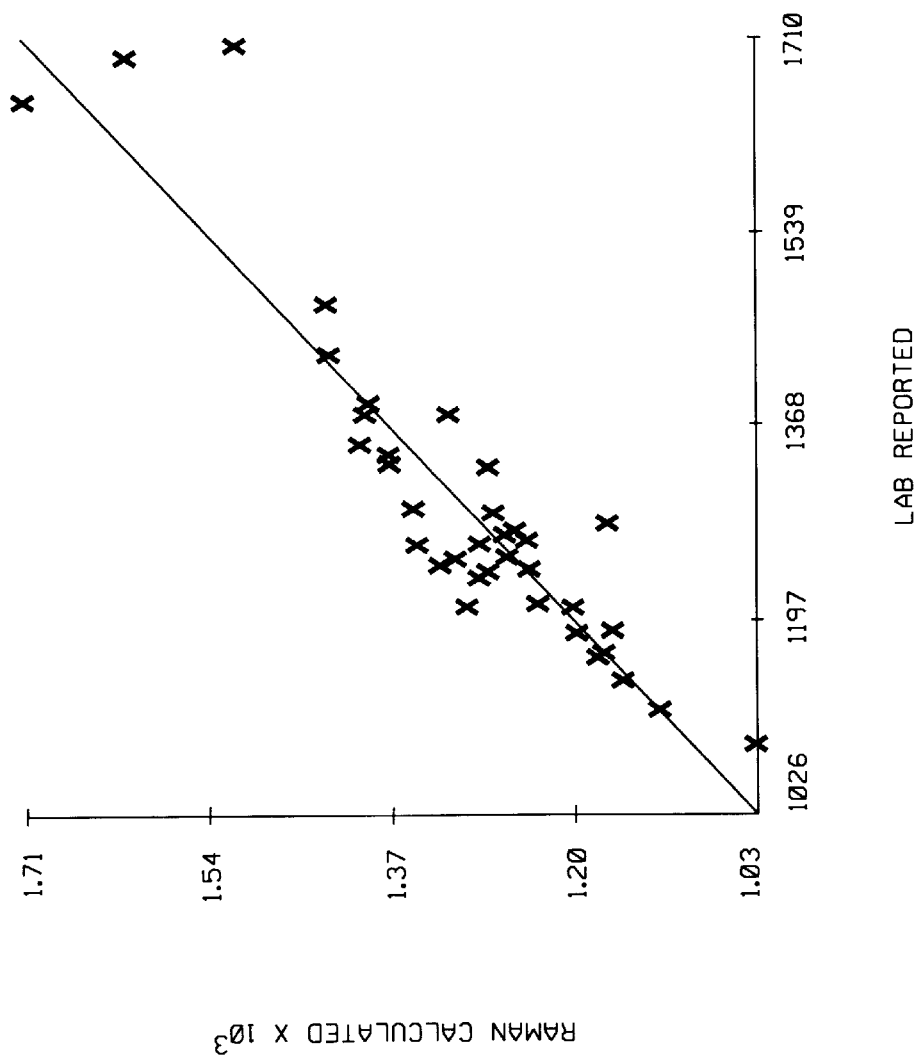
Figure 12:
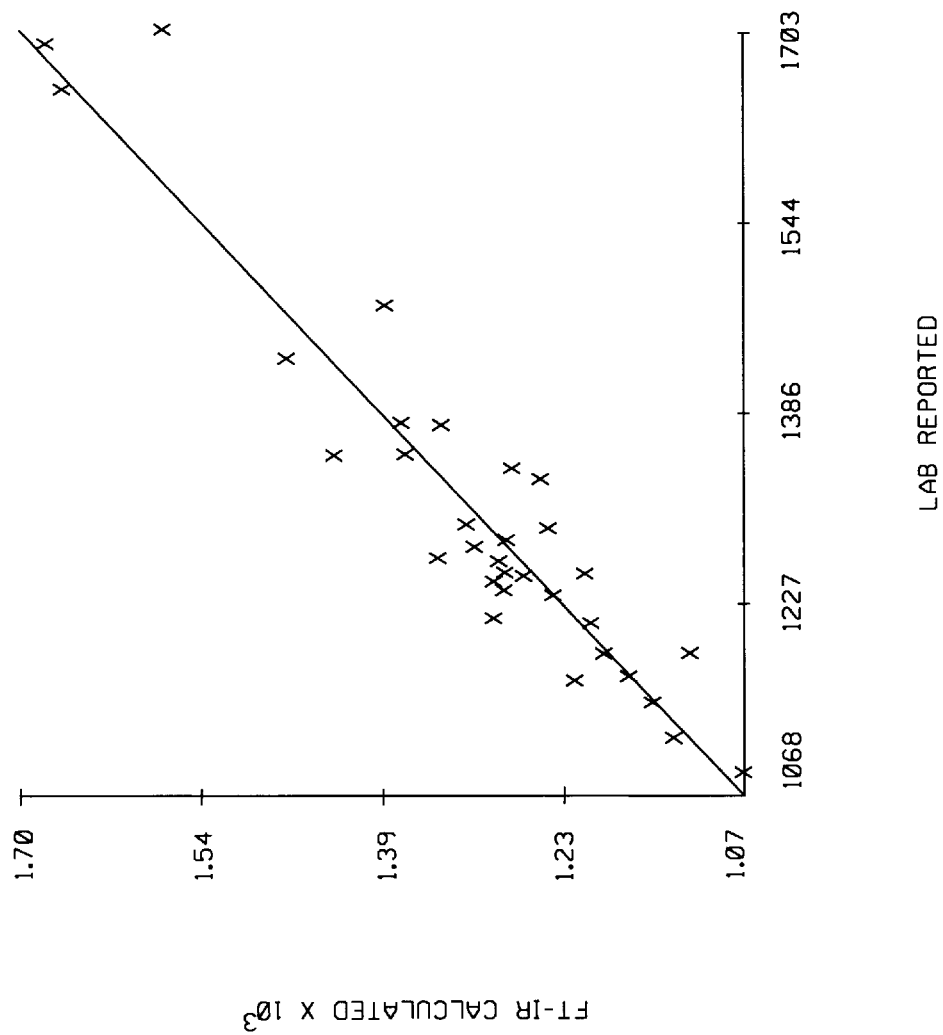

Table I sets forth the methods for boiling point and distillation properties of neat gasolines taken from a set of approximately 110 samples which shows the range (highest and lowest) sample value, the mathematical average, the offset constant, k(0) and constants k(1), k(2) and k(3) which are to be multiplied with the absorbance at wavelengths 1, 2 and 3, respectively. The R-value and $R^2$-values are measures of the error and the NIR standard error is actually the standard error of estimates (SE or SEE). The first set of data in Table 1 uses multiple linear regression (MLR) while the second set uses partial least squares (PLS).

Table II is similar to Table I except that it covers MTBE gasolines.

Table III is similar to Table I except that it utilizes Mid-IR.

Table IV is similar to Table I except that it relates to determination of distillation properties of neat gasolines by Raman.

Table V is similar to Table I except that it relates to determination of distillation properties of MTBE gasolines by Raman.

Table VI is similar to Table I except that it relates to determination of EPA parameters for winter gasolines by NIR.

Table VII is similar to Table I except that it relates to determination of EPA parameters of summer gasolines by NIR.

Table VIII is similar to Table I except that it relates to determination of EPA parameters of winter gasolines by Mid-IR.

Table IX is similar to Table I except that it relates to determination of EPA parameters of summer gasolines by Mid-IR.

Table X is similar to Table I except that it relates to determination of EPA parameters for winter gasolines by Raman.

Table XI is similar to Table I except that it relates to determination of EPA parameters for summer gasolines by Raman.

Table XII is similar to Table I except that it covers the driveability index of gasolines of various "gasoline types" (See far left column) by Near-IR, Mid-IR, and Raman spectroscopy (as indicated in the subheadings).

Table XIII is a table relating the error in the primary (conventional) methods for distillation, sulfur, aromatics, olefins, benzene, and oxygenates, to the possible errors for the EPA complex model fuel parameters.

TABLE I

Statistics For Distillation Correlations of Neat Gasolines By NIR

Multiple Linear Regression Equations For Distillation Parameters

| Property | Primary Method | Range | Average | CONSTANTS | | | |
| --- | --- | --- | --- | --- | --- | --- | --- |
| | | | | K (0) | K (1) | K (2) | K (3) |
| Initial Boiling Point | ASTM D 3710 | 50.87–130.67 | 85.662 | 350.032 | −827.077 | −491.667 | 349.315 |
| 10% | ASTM D 3710 | 66.13–187.24 | 105.076 | 756.536 | 853.319 | −886.699 | −869.293 |
| 20% | ASTM D 3710 | 84.66–214.57 | 130.624 | 541.348 | 494.852 | −495.969 | −946.904 |
| 30% | ASTM D 3710 | 105.11–238.14 | 152.861 | 848.502 | 877.772 | −756.635 | 710.65 |
| 50% | ASTM D 3710 | 149.72–278.77 | 198.504 | 467.516 | −946.696 | 491.731 | 524.197 |
| 70% | ASTM D 3710 | 225.75–314.89 | 262.184 | 177.875 | −195.956 | −132.206 | 717.695 |
| 80% | ASTM D 3710 | 259.72–335.49 | 297.912 | 246.825 | 386.051 | 167.859 | 261.022 |
| 90% | ASTM D 3710 | 305.65–377.58 | 342.029 | 443.341 | −482.256 | 328.742 | 294.823 |
| End Point | ASTM D 3710 | 371.43–461.74 | 422.972 | 345.968 | 806.877 | −660.697 | 482.001 |
| Vol % Dist @ 200 F. | ASTM D 3710 | 14.669–63.226 | 49.001 | −124.272 | 437.539 | 185.162 | −293.333 |
| Vol % Dist @ 300 F. | ASTM D 3710 | 61.755–88.571 | 79.26 | 148.001 | −259.096 | −56.041 | −304.617 |

Multiple Linear Regression Equations For Distillation Parameters

| Property | WAVELENGTHS | | | R | $R^2$ | NIR Std. Error |
| --- | --- | --- | --- | --- | --- | --- |
| | 1 | 2 | 3 | | | |
| Initial Boiling Point | 1226 | 2078 | 1820 | 0.8757 | 0.7669 | 7.48 |
| 10% | 1198 | 1848 | 2182 | 0.8555 | 0.7319 | 10.6 |
| 20% | 1828 | 2080 | 1228 | 0.9186 | 0.8438 | 9.01 |
| 30% | 2060 | 1802 | 1204 | 0.9430 | 0.8892 | 7.83 |
| 50% | 1860 | 1628 | 1148 | 0.8964 | 0.8035 | 10.8 |
| 70% | 2154 | 1642 | 2060 | 0.8965 | 0.8037 | 10.3 |
| 80% | 1818 | 1176 | 2126 | 0.8551 | 0.7312 | 10.7 |
| 90% | 1614 | 1814 | 1178 | 0.8026 | 0.6442 | 8.17 |
| End Point | 1160 | 1598 | 1816 | 0.7057 | 0.4980 | 12.2 |
| Vol % Dist @ 200 F. | 1238 | 1804 | 2066 | 0.9368 | 0.8776 | 3.06 |
| Vol % Dist @ 300 F. | 1158 | 1812 | 2062 | 0.9086 | 0.8256 | 2.3 |

PLS Equations For Distillation Parameters

| Property | Primary Method | Range | Average | Wavelength Range (nm) |
| --- | --- | --- | --- | --- |
| Initial Boiling Point | ASTM D 3710 | 50.87–130.67 | 85.415 | 1214–1264, 2050–2100, 1780–1860 |
| 10% | ASTM D 3710 | 66.13–187.24 | 105.076 | 1156–1214, 1780–1860, 2160–2200 |
| 20% | ASTM D 3710 | 84.66–214.57 | 130.624 | 1142–1166, 1206–1264, 1660–1670, 1780–1860, 2050–2094 |
| 30% | ASTM D 3710 | 105.11–238.14 | 152.861 | 1144–1242, 1800–1864, 2000–2100 |
| 50% | ASTM D 3710 | 149.72–278.77 | 198.504 | 1780–1900, 1600–1670, 1140–1214 |
| 70% | ASTM D 3710 | 225.75–314.89 | 262.184 | 1608–1666, 2000–2196 |
| 80% | ASTM D 3710 | 259.72–335.49 | 297.912 | 1156–1226, 1780–1856, 2112–2160 |
| 90% | ASTM D 3710 | 305.65–377.58 | 342.029 | 1142–1214, 1578–1662, 1790–1860 |
| End Point | ASTM D 3710 | 371.43–461.74 | 422.972 | 1140–1214, 1560–1630, 1780–1866 |
| Vol % Dist @ 200 F. | ASTM D 3710 | 14.669–63.226 | 49.001 | 1214–1264, 1780–1860, 2030–2100 |
| Vol % Dist @ 300 F. | ASTM D 3710 | 61.755–88.571 | 79.26 | 1140–1214, 1780–1860, 2030–2100 |

PLS Equations For Distillation Parameters

| Property | Factors | R | $R^2$ | NIR Std. Error |
| --- | --- | --- | --- | --- |
| Initial Boiling Point | 3 | 0.8581 | 0.7363 | 7.96 |
| 10% | 5 | 0.8764 | 0.7681 | 9.91 |
| 20% | 6 | 0.9395 | 0.8827 | 7.90 |
| 30% | 7 | 0.9652 | 0.9316 | 6.25 |
| 50% | 4 | 0.8840 | 0.7815 | 11.49 |
| 70% | 8 | 0.9338 | 0.8720 | 8.51 |
| 80% | 11 | 0.9263 | 0.8580 | 8.05 |
| 90% | 11 | 0.9043 | 0.8178 | 6.04 |
| End Point | 10 | 0.8122 | 0.6597 | 10.37 |
| Vol % Dist @ 200 F. | 7 | 0.9484 | 0.8994 | 2.82 |
| Vol % Dist @ 300 F. | 3 | 0.9060 | 0.8208 | 2.34 |

Initial through end points are in degrees Fahrenheit.

TABLE II

Statistics For Distillation Correlations of MTBE Gasolines By NIR

Multiple Linear Regression Equations For Distillation Parameters

| Property | Primary Method | Range | Average | CONSTANTS | | | |
|---|---|---|---|---|---|---|---|
| | | | | K (0) | K (1) | K (2) | K (3) |
| Initial Boiling Point | ASTM D 3710 | 66.45–105.37 | 86.246 | 381.137 | −585.282 | −805.925 | −123.733 |
| 10% | ASTM D 3710 | 80.24–133.29 | 105.600 | 298.181 | −1660.32 | 1279.83 | −246.043 |
| 20% | ASTM D 3710 | 99.45–155.53 | 127.408 | 188.89 | 234.404 | 794.044 | −992.336 |
| 30% | ASTM D 3710 | 119.67–190.57 | 146.713 | 224.173 | −336.566 | −977.518 | 248.875 |
| 50% | ASTM D 3710 | 142.67–277.66 | 185.149 | 340.641 | 674.775 | 689.043 | −600.835 |
| 70% | ASTM D 3710 | 200.88–310.70 | 242.015 | 166.84 | −562.526 | 298.943 | 270.773 |
| 80% | ASTM D 3710 | 228.93–337.08 | 279.224 | 223.942 | −391.06 | −569.825 | −232.691 |
| 90% | ASTM D 3710 | 288.61–377.97 | 334.335 | 300.678 | −122.157 | 703.648 | −150.516 |
| End Point | ASTM D 3710 | 384.78–455.14 | 419.087 | 613.754 | −849.991 | −100.541 | 723.589 |
| Vol % Dist @ 200 F. | ASTM D 3710 | 32.166–69.698 | 54.661 | 130.875 | 470.12 | 776.943 | 331.167 |
| Vol % Dist @ 300 F. | ASTM D 3710 | 63.523–91.000 | 82.961 | 5.733 | 278.857 | 79.714 | 149.008 |

Multiple Linear Regression Equations For Distillation Parameters

| Property | WAVELENGTHS | | | R | $R^2$ | NIR Std. Error |
|---|---|---|---|---|---|---|
| | 1 | 2 | 3 | | | |
| Initial Boiling Point | 1230 | 1850 | 2092 | 0.9251 | 0.8558 | 5.66 |
| 10% | 1228 | 1940 | 1390 | 0.8927 | 0.7969 | 8.49 |
| 20% | 1828 | 2056 | 1978 | 0.8957 | 0.8023 | 6.38 |
| 30% | 1200 | 1238 | 1830 | 0.8986 | 0.8075 | 6.82 |
| 50% | 1178 | 1214 | 2040 | 0.8474 | 0.7181 | 12.8 |
| 70% | 1152 | 1812 | 2130 | 0.9268 | 0.8590 | 8.7 |
| 80% | 1236 | 2016 | 2166 | 0.9084 | 0.8252 | 10.6 |
| 90% | 1794 | 2052 | 2164 | 0.8901 | 0.7923 | 7.75 |
| End Point | 1228 | 1642 | 2046 | 0.7447 | 0.5546 | 12.8 |
| Vol % Dist @ 200 F. | 1188 | 1154 | 1800 | 0.9170 | 0.8409 | 3.03 |
| Vol % Dist @ 300 F. | 1158 | 1788 | 2086 | 0.9419 | 0.8872 | 1.63 |

PLS Equations For Distillation Parameters

| Property | Primary Method | Range | Average | Wavelength Range (nm) |
|---|---|---|---|---|
| Initial Boiling Point | ASTM D 3710 | 66.45–105.37 | 86.246 | 1214–1264, 1780–1860, 2050–2160 |
| 10% | ASTM D 3710 | 80.24–133.29 | 105.600 | 1214–1264, 1320–1430, 1900–1970 |
| 20% | ASTM D 3710 | 99.45–155.53 | 127.408 | 1780–1860, 1950–2100 |
| 30% | ASTM D 3710 | 119.67–190.57 | 146.713 | 1156–1264, 1780–1860 |
| 50% | ASTM D 3710 | 142.67–277.66 | 185.149 | 1156–1230, 2000–2100 |
| 70% | ASTM D 3710 | 200.88–310.70 | 242.015 | 1140–1214, 1780–1860, 2100–2160 |
| 80% | ASTM D 3710 | 228.93–337.08 | 279.224 | 1214–1264, 2000–2040, 2100–2200 |
| 90% | ASTM D 3710 | 288.61–377.97 | 334.335 | 1780–1860, 2000–2200 |
| End Point | ASTM D 3710 | 384.78–455.14 | 419.087 | 1214–1264, 1600–1670, 2000–2100 |
| Vol % Dist @ 200 F. | ASTM D 3710 | 32.166–69.698 | 54.661 | 1140–1214, 1780–1860 |
| Vol % Dist @ 300 F. | ASTM D 3710 | 63.523–91.000 | 82.961 | 1140–1214, 1780–1860, 2050–2100 |

PLS Equations For Distillation Parameters

| Property | Factors | R | $R^2$ | NIR Std. Error |
|---|---|---|---|---|
| Initial Boiling Point | 5 | 0.9291 | 0.8632 | 5.59 |
| 10% | 5 | 0.9019 | 0.8134 | 8.26 |
| 20% | 6 | 0.9574 | 0.9166 | 4.23 |
| 30% | 9 | 0.9602 | 0.9220 | 4.54 |
| 50% | 6 | 0.9178 | 0.8424 | 9.80 |
| 70% | 4 | 0.9184 | 0.8435 | 9.23 |
| 80% | 10 | 0.9625 | 0.9264 | 7.29 |
| 90% | 10 | 0.9655 | 0.9322 | 4.67 |
| End Point | 10 | 0.9136 | 0.8347 | 8.20 |
| Vol % Dist @ 200 F. | 7 | 0.9216 | 0.8493 | 3.03 |
| Vol % Dist @ 300 F. | 6 | 0.9447 | 0.8925 | 1.63 |

Initial through end points are in degrees Fahrenheit.

TABLE III

Statistics For Distillation Equations of Neat Gasolines By Mid-IR

Multiple Linear Regression Equations For EPA Parameters

| Property | Primary Method | Range | Average | K (0) | K (1) | K (2) | K (3) |
|---|---|---|---|---|---|---|---|
| Initial Boiling Point | ASTM D 3710 | 50.87–130.67 | 85.415 | 115.680 | −777.376 | 1333.380 | −2527.993 |
| 10% | ASTM D 3710 | 66.13–187.24 | 104.751 | 88.740 | −1784.502 | −2286.500 | 2568.906 |
| 20% | ASTM D 3710 | 84.66–214.57 | 130.075 | 191.305 | −1842.247 | 540.681 | 1333.962 |
| 30% | ASTM D 3710 | 105.11–238.14 | 152.342 | 164.429 | −1398.272 | −925.467 | 1386.218 |
| 50% | ASTM D 3710 | 149.72–278.77 | 198.321 | 144.105 | 1635.984 | −1033.755 | 1455.084 |
| 70% | ASTM D 3710 | 225.75–314.89 | 262.07 | 274.502 | −561.602 | 1311.308 | 2027.270 |
| 80% | ASTM D 3710 | 259.72–335.49 | 297.588 | 296.646 | 619.257 | 177.189 | −1382.259 |
| 90% | ASTM D 3710 | 305.65–377.58 | 341.791 | 331.132 | −1526.334 | −345.944 | −2406.509 |
| End Point | ASTM D 3710 | 371.43–461.74 | 422.382 | 396.507 | 1004.513 | −3340.712 | 2824.264 |
| Vol % Dist @ 200 F. | ASTM D 3710 | 14.669–63.226 | 49.162 | 54.241 | 438.117 | −412.188 | 336.432 |
| Vol % Dist @ 300 F. | ASTM D 3710 | 61.755–88.571 | 79.28 | 78.589 | 147.237 | 113.544 | −728.699 |

Multiple Linear Regression Equations For EPA Parameters

| | WAVENUMBERS | | | | | Mid-IR |
|---|---|---|---|---|---|---|
| Property | 1 | 2 | 3 | R | $R^2$ | Std. Error |
| Initial Boiling Point | 951.9 | 2892.4 | 0.8671 | 0.7519 | 7.82 | |
| 10% | 2904 | 2877 | 948.1 | 0.8549 | 0.7309 | 10.60 |
| 20% | 2896.3 | 1411 | 959.6 | 0.8788 | 0.7723 | 10.80 |
| 30% | 2896.3 | 1488.2 | 1391.7 | 0.9012 | 0.8122 | 10.10 |
| 50% | 1565.3 | 1345.4 | 867.1 | 0.8707 | 0.7581 | 11.90 |
| 70% | 2992.7 | 1399.4 | 870.9 | 0.9046 | 0.8183 | 9.97 |
| 80% | 2865.4 | 1565.3 | 801.5 | 0.8594 | 0.7386 | 10.70 |
| 90% | 797.6 | 747.5 | 3066 | 0.8292 | 0.6876 | 7.85 |
| End Point | 944.2 | 801.5 | 805.3 | 0.7352 | 0.5405 | 11.90 |
| Vol % Dist @ 200 F. | 1488.2 | 1395.6 | 2900.2 | 0.9054 | 0.8197 | 3.73 |
| Vol % Dist @ 300 F. | 2900.2 | 797.6 | 867 | 0.9141 | 0.8356 | 2.25 |

PLS Equations For EPA Parameters

| Property | Primary Method | Range | Average | Wavelength Range (cm − 1) |
|---|---|---|---|---|
| Initial Boiling Point | ASTM D 3710 | 50.87–130.67 | 85.415 | 3069.9–2738.1 |
| 10% | ASTM D 3710 | 66.13–187.24 | 104.751 | 2931–2842.3, 971.2–743.6 |
| 20% | ASTM D 3710 | 84.66–214.57 | 130.075 | 3162.5–2734.3, 2352.3–2240.5, 1654.1–689.6 |
| 30% | ASTM D 3710 | 105.11–238.14 | 152.342 | 3147.1–2722.7, 1573–689.6 |
| 50% | ASTM D 3710 | 149.72–278.77 | 198.321 | 2904–2900.2, 2348.5–2282.9, 1607.8–1522.9, 1395.6–1303. |
| 70% | ASTM D 3710 | 225.75–314.89 | 262.07 | 3054.5–2823, 1445.7–1306.6, 936.5–832.3 |
| 80% | ASTM D 3710 | 259.72–335.49 | 297.588 | 3093–2726.5, 1781.4–720.4 |
| 90% | ASTM D 3710 | 305.65–377.58 | 341.791 | 3093–2726.5, 1781.4–720.4 |
| End Point | ASTM D 3710 | 371.43–461.74 | 422.382 | 3093–2726.5, 1781.4–720.4 |
| Vol % Dist @ 200 F. | ASTM D 3710 | 14.669–63.226 | 49.162 | 3093–2726.5, 1781.4–720.4 |
| Vol % Dist @ 300 F. | ASTM D 3710 | 61.755–88.571 | 79.28 | 3093–2726.5, 1781.4–720.4 |

PLS Equations For EPA Parameters

| Property | Factors | R | $R^2$ | Mid-IR Std. Error |
|---|---|---|---|---|
| Initial Boiling Point | 11 | 0.887 | 0.7880 | 7.488 |
| 10% | 7 | 0.9054 | 0.8197 | 8.850 |
| 20% | 9 | 0.9234 | 0.8527 | 8.894 |
| 30% | 8 | 0.9384 | 0.8806 | 8.218 |
| 50% | 4 | 0.9000 | 0.8100 | 10.528 |
| 70% | 10 | 0.9456 | 0.8942 | 7.878 |
| 80% | 6 | 0.8633 | 0.7453 | 10.705 |
| 90% | 12 | 0.9317 | 0.8681 | 5.317 |
| End Point | 13 | 0.8986 | 0.8075 | 8.052 |
| Vol % Dist @ 200 F. | 8 | 0.9435 | 0.8902 | 2.979 |
| Vol % Dist @ 300 F. | 7 | 0.9357 | 0.8755 | 1.995 |

Initial through end points are in degrees Fahrenheit.

TABLE IV

Statistics For Distillation Equations of NEAT Gasolines By RAMAN

Multiple Linear Regression Equations For Distillation Parameters

| Property | Primary Method | Range | Average | CONSTANTS | | | |
|---|---|---|---|---|---|---|---|
| | | | | K (0) | K (1) | K (2) | K (3) |
| Initial Boiling Point | ASTM D 3710 | 50.87–130.67 | 85.415 | 78.651 | 144.051 | 205.871 | −263.998 |
| 10% | ASTM D 3710 | 66.13–187.24 | 104.751 | 114.843 | 34.434 | 324.925 | −367.699 |
| 20% | ASTM D 3710 | 84.66–214.57 | 130.075 | 162.660 | 461.811 | −311.060 | −180.121 |
| 30% | ASTM D 3710 | 105.11–238.14 | 152.342 | 167.398 | 463.549 | −190.640 | −169.186 |
| 50% | ASTM D 3710 | 149.72–278.77 | 198.321 | 206.963 | −565.834 | −197.504 | 809.524 |
| 70% | ASTM D 3710 | 225.75–314.89 | 262.07 | 276.240 | −13.898 | 185.143 | −209.203 |
| 80% | ASTM D 3710 | 259.72–335.49 | 297.588 | 291.839 | −209.878 | −89.502 | 342.898 |
| 90% | ASTM D 3710 | 305.65–377.58 | 341.791 | 326.796 | 194.670 | −182.944 | −70.395 |
| End Point | ASTM D 3710 | 371.43–461.74 | 422.382 | 401.834 | −11.951 | −193.552 | 254.718 |
| Vol % Dist @ 200 F. | ASTM D 3710 | 14.669–63.226 | 49.162 | 56.467 | 64.089 | −138.582 | 86.031 |
| Vol % Dist @ 300 F. | ASTM D 3710 | 61.755–88.571 | 79.28 | 85.049 | −24.833 | 84.438 | −68.473 |

Multiple Linear Regression Equations For Distillation Parameters

| Property | WAVENUMBERS | | | | | RAMAN |
|---|---|---|---|---|---|---|
| | 1 | 2 | 3 | R | $R^2$ | Std. Error |
| Initial Boiling Point | 1025.3 | 898.1 | 840.2 | 0.8569 | 0.7343 | 8.07 |
| 10% | 998.3 | 898.1 | 840.2 | 0.8799 | 0.7742 | 9.84 |
| 20% | 1160.3 | 840.2 | 797.8 | 0.9174 | 0.8416 | 9.27 |
| 30% | 1198.9 | 840.2 | 797.8 | 0.9280 | 0.8612 | 8.95 |
| 50% | 385.1 | 1430.3 | 254 | 0.9079 | 0.8243 | 10.60 |
| 70% | 2919.1 | 1384 | 793.9 | 0.9155 | 0.8381 | 9.57 |
| 80% | 813.2 | 2996.3 | 1387.9 | 0.8908 | 0.7935 | 9.52 |
| 90% | 1376.3 | 813.2 | 998.3 | 0.9043 | 0.8178 | 5.92 |
| End Point | 2919.1 | 1611.6 | 1384 | 0.8381 | 0.7024 | 9.50 |
| Vol % Dist @ 200 F. | 793.9 | 516.2 | 385.1 | 0.9212 | 0.8486 | 3.48 |
| Vol % Dist @ 300 F. | 1384 | 813.2 | 550.9 | 0.9291 | 0.8632 | 2.10 |

PLS Equations For Distillation Parameters

| Property | Primary Method | Range | Average | Wavelength Range (cm − 1) |
|---|---|---|---|---|
| Initial Boiling Point | ASTM D 3710 | 50.87–130.67 | 85.415 | 3046.4–2710.8, 2321.9–419.8 |
| 10% | ASTM D 3710 | 66.13–187.24 | 104.751 | 3046.4–2710.8, 1681–292.5 |
| 20% | ASTM D 3710 | 84.66–214.57 | 130.075 | 1168.1–1137.2, 894.2–751.5 |
| 30% | ASTM D 3710 | 105.11–238.14 | 152.342 | 3058–2710.8, 1681–254 |
| 50% | ASTM D 3710 | 149.72–278.77 | 198.321 | 1484.3–223.1 |
| 70% | ASTM D 3710 | 225.75–314.89 | 262.07 | 3069.5–2710.8, 1627–230.8 |
| 80% | ASTM D 3710 | 259.72–335.49 | 297.588 | 3050.3–2753.3, 1669.5–227 |
| 90% | ASTM D 3710 | 305.65–377.58 | 341.791 | 3096.5–2753.3, 1681–207.7 |
| End Point | ASTM D 3710 | 371.43–461.74 | 422.382 | 3058–2734, 1681–200 |
| Vol % Dist @ 200 F. | ASTM D 3710 | 14.669–63.226 | 49.162 | 3096.5–2764.8, 1681–223.1 |
| Vol % Dist @ 300 F. | ASTM D 3710 | 61.755–88.571 | 79.28 | 3004–2710.8, 1681–200 |

PLS Equations For Distillation Parameters

| Property | Factors | R | $R^2$ | RAMAN Std. Error |
|---|---|---|---|---|
| Initial Boiling Point | 6 | 0.8961 | 0.8030 | 7.037 |
| 10% | 6 | 0.9049 | 0.8188 | 8.928 |
| 20% | 4 | 0.9337 | 0.8718 | 8.382 |
| 30% | 6 | 0.9495 | 0.9016 | 7.633 |
| 50% | 2 | 0.8715 | 0.7595 | 12.315 |
| 70% | 6 | 0.9287 | 0.8625 | 8.944 |
| 80% | 6 | 0.9050 | 0.8190 | 9.030 |
| 90% | 8 | 0.9451 | 0.8932 | 4.632 |
| End Point | 8 | 0.9094 | 0.8270 | 7.407 |
| Vol % Dist @ 200 F. | 5 | 0.9382 | 0.8802 | 3.126 |
| Vol % Dist @ 300 F. | 6 | 0.9459 | 0.8947 | 1.865 |

Initial through end points are in degrees Fahrenheit.

TABLE V

Statistics For Distillation Equations of MTBE Gasolines By RAMAN

Multiple Linear Regression Equations For Distillation Parameters

| Property | Primary Method | Range | Average | CONSTANTS | | | |
|---|---|---|---|---|---|---|---|
| | | | | K (0) | K (1) | K (2) | K (3) |
| Initial Boiling Point | ASTM D 3710 | 66.45–105.37 | 86.423 | 117.475 | 227.230 | 568.743 | −429.493 |
| 10% | ASTM D 3710 | 80.24–133.29 | 105.796 | 123.578 | 233.993 | −583.105 | 333.398 |
| 20% | ASTM D 3710 | 99.45–155.53 | 127.563 | 181.176 | −240.985 | −172.335 | 230.593 |
| 30% | ASTM D 3710 | 119.67–190.57 | 146.895 | 129.841 | −202.985 | −183.989 | 431.758 |
| 50% | ASTM D 3710 | 142.67–277.66 | 185.528 | 145.298 | −97.209 | 72.455 | 419.539 |
| 70% | ASTM D 3710 | 200.88–310.70 | 242.031 | 254.819 | 499.101 | −46.339 | 352.621 |
| 80% | ASTM D 3710 | 228.93–337.08 | 279.094 | 307.769 | −47.342 | 91.989 | 589.017 |
| 90% | ASTM D 3710 | 288.61–377.97 | 334.185 | 352.329 | −20.561 | 365.209 | −382.598 |
| End Point | ASTM D 3710 | 384.78–455.14 | 419.07 | 410.292 | 260.958 | −777.788 | 129.851 |
| Vol % Dist @ 200 F. | ASTM D 3710 | 32.166–69.698 | 54.606 | 60.008 | 219.237 | −157.971 | −91.578 |
| Vol % Dist @ 300 F. | ASTM D 3710 | 63.523–91.000 | 83.011 | 81.770 | 4.505 | −90.417 | 27.392 |

Multiple Linear Regression Equations For Distillation Parameters

| Property | WAVENUMBERS | | | R | $R^2$ | RAMAN Std. Error |
|---|---|---|---|---|---|---|
| | 1 | 2 | 3 | | | |
| Initial Boiling Point | 1021.5 | 689.8 | 431.4 | 0.8959 | 0.8026 | 6.61 |
| 10% | 1021.5 | 431.4 | 307.9 | 0.9098 | 0.8277 | 7.96 |
| 20% | 840.2 | 797.8 | 246.2 | 0.9378 | 0.8795 | 5.10 |
| 30% | 840.2 | 759.2 | 311.8 | 0.9353 | 0.8748 | 5.64 |
| 50% | 2942.3 | 2911.4 | 307.9 | 0.9222 | 0.8505 | 9.48 |
| 70% | 1326.2 | 2942.3 | 242.4 | 0.9392 | 0.8821 | 8.20 |
| 80% | 2942.3 | 1384 | 1330 | 0.9201 | 0.8466 | 10.20 |
| 90% | 2973.1 | 1372.5 | 1052.3 | 0.9213 | 0.8488 | 6.73 |
| End Point | 1376.3 | 1052.3 | 766.9 | 0.9035 | 0.8163 | 8.33 |
| Vol % Dist @ 200 F. | 1488.2 | 311.8 | 516.2 | 0.9231 | 0.8521 | 2.99 |
| Vol % Dist @ 300 F. | 2938.4 | 1372.5 | 1009.9 | 0.9553 | 0.9126 | 1.48 |

PLS Equations For Distillation Parameters

| Property | Primary Method | Range | Average | Wavelength Range (cm − 1) |
|---|---|---|---|---|
| Initial Boiling Point | ASTM D 3710 | 66.45–105.37 | 86.423 | 3038.7–2795.7, 1665.6–200 |
| 10% | ASTM D 3710 | 80.24–133.29 | 105.796 | 2953.8–2734, 1681–200 |
| 20% | ASTM D 3710 | 99.45–155.53 | 127.563 | 3031–2818.8, 1673.3–200 |
| 30% | ASTM D 3710 | 119.67–190.57 | 146.895 | 3096.5–2710.8, 1681–200 |
| 50% | ASTM D 3710 | 142.67–277.66 | 185.528 | 2980.8–2869, 346.5–269.4 |
| 70% | ASTM D 3710 | 200.88–310.70 | 242.031 | 2984.7–2926.8, 1403.3–1276.1 |
| 80% | ASTM D 3710 | 228.93–337.08 | 279.094 | 3000.1–2903.7, 1422.6–1279.9 |
| 90% | ASTM D 3710 | 288.61–377.97 | 334.185 | 3046.4–2710.8, 1681–207.7 |
| End Point | ASTM D 3710 | 384.78–455.14 | 419.07 | 3096.5–2734, 1673.3–207.7 |
| Vol % Dist @ 200 F. | ASTM D 3710 | 32.166–69.698 | 54.606 | 3000.1–2710.8, 1657.9–219.2 |
| Vol % Dist @ 300 F. | ASTM D 3710 | 63.523–91.000 | 83.011 | 3073.4–2726.3, 1673.3–207.7 |

PLS Equations For Distillation Parameters

| Property | Factors | R | $R^2$ | RAMAN Std. Error |
|---|---|---|---|---|
| Initial Boiling Point | 7 | 0.9115 | 0.8308 | 6.3260 |
| 10% | 7 | 0.9304 | 0.8656 | 7.2641 |
| 20% | 8 | 0.9761 | 0.9528 | 3.3233 |

TABLE V-continued

Statistics For Distillation Equations of MTBE Gasolines By RAMAN

| | | | | |
|---|---|---|---|---|
| 30% | 9 | 0.9846 | 0.9694 | 2.9241 |
| 50% | 5 | 0.9323 | 0.8692 | 9.0030 |
| 70% | 3 | 0.9217 | 0.8495 | 9.2717 |
| 80% | 4 | 0.9083 | 0.8250 | 10.9990 |
| 90% | 9 | 0.9734 | 0.9475 | 4.1645 |
| End Point | 9 | 0.9608 | 0.9231 | 5.6621 |
| Vol % Dist @ 200 F. | 6 | 0.9512 | 0.9048 | 2.4604 |
| Vol % Dist @ 300 F. | 8 | 0.9754 | 0.9514 | 1.1466 |

Initial through end points are in degrees Fahrenheit.

TABLE VI

EPA Parameters of Winter Gasolines by NIR

Multiple Linear Regression Equations For EPA Parameters

| Parameter | Range | Average | CONSTANTS | | | | WAVELENGTHS | | | R | $R^2$ | NIR STD ERROR |
|---|---|---|---|---|---|---|---|---|---|---|---|---|
| | | | K (0) | K (1) | K (2) | K (3) | 1 | 2 | 3 | | | |
| Exhaust Benzene | 3515–9.403 | 5.421 | 1.081 | −9.127 | −11.517 | −19.382 | 2022 | 2136 | 2180 | 0.9574 | 0.9166 | 0.266 |
| Total Toxics | 18.572–23.981 | 20.118 | 21.844 | −82.816 | −34.182 | −8.780 | 1470 | 1928 | 2136 | 0.9473 | 0.8974 | 0.275 |
| Exhaust Benzene | 16.695–57.557 | 30.740 | 63.663 | 264.987 | −79.321 | −98.160 | 1430 | 1800 | 2132 | 0.8581 | 0.7363 | 3.260 |
| Total Toxics | 36.694–79.611 | 52.426 | 107.888 | 708.106 | −142.487 | −110.377 | 1434 | 1802 | 2132 | 0.8562 | 0.7331 | 3.770 |
| $NO_x$ | 645.836–885.410 | 749.708 | 1312.388 | −988.749 | 1289.229 | 1411.569 | 1790 | 1836 | 2032 | 0.919 | 0.8446 | 22.300 |
| Total VOC | 578.163–1184.666 | 680.413 | 2756.248 | −9191.208 | −1860.146 | 1497.272 | 1462 | 1654 | 2062 | 0.8643 | 0.7470 | 46.800 |
| Exhaust Benzene | 34.804–116.108 | 63.176 | 220.618 | 250.674 | 438.936 | −709.153 | 1178 | 1834 | 1908 | 0.8841 | 0.7816 | 5.930 |
| Total Toxics | 75.756–161.127 | 107.929 | 327.050 | 523.932 | −535.690 | 454.169 | 1176 | 1620 | 1830 | 0.8824 | 0.7786 | 6.880 |
| $NO_x$ | 1324.24–1843.13 | 1542.669 | 1564.034 | 3408.109 | 8450.706 | −2348.445 | 1420 | 1592 | 1794 | 0.9188 | 0.8442 | 46.600 |
| Total VOC | 1186.917–2367.174 | 1377.457 | 3610.603 | 93817.390 | −3066.116 | −45905.830 | 1574 | 1652 | 1462 | 0.8869 | 0.7866 | 82.700 |

PLS Equations for EPA Parameters

| Parameter | Range | Average | Wavelength Range (nm) | Factors | R | $R^2$ | |
|---|---|---|---|---|---|---|---|
| Exhaust Benzene | 3.515–9.403 | 5.421 | 1156–1214, 1600–1670, 2100–2162 | 12 | 0.9840 | 0.9683 | 0.172 |
| Total Toxics | 18.572–23.981 | 20.118 | 1156–1214, 1600–1670, 2100–2162 | 13 | 0.9825 | 0.9653 | 0.168 |
| Exhaust Benzene | 16.695–57.557 | 30.740 | 1132–1214, 1600–1670 | 12 | 0.9474 | 0.8976 | 2.104 |
| Total Toxics | 36.694–79.611 | 52.426 | 1400–1480, 1600–1670, 1780–1860, 2100–2160 | 13 | 0.9425 | 0.8883 | 2.534 |
| $NO_x$ | 645.836–885.410 | 749.708 | 1214–1230, 1480–1630, 1780–1860, 2000–2050, 2100–2200 | 9 | 0.9568 | 0.9155 | 16.849 |
| Total VOC | 578.163–1184.666 | 680.413 | 1142–1148, 1172–1256, 1420–1426, 1594–1670 | 10 | 0.9081 | 0.8246 | 40.001 |
| Exhaust Benzene | 34.804–116.108 | 63.176 | 1140–1214, 1550–1670, 1780–1860, 1890–1930, 2100–2200 | 13 | 0.9410 | 0.8855 | 4.466 |
| Total Toxics | 75.756–161.127 | 107.929 | 1156–1214, 1350–1520, 1600–1670, 1950–2020, 2100–2200 | 11 | 0.9252 | 0.8560 | 5.724 |
| $NO_x$ | 1324.24–1843.13 | 1542.669 | 1156–1214, 1400–1450, 1570–1630, 1780–1860 | 13 | 0.9603 | 0.9222 | 34.296 |
| Total VOC | 1186.917–2367.174 | 1377.457 | 1138–1252, 1560–1670, 1780–1784 | 11 | 0.9270 | 0.8593 | 69.202 |

TABLE VII

EPA Parameters of Summer Gasolines by NIR

Multiple Linear Regression Equations For EPA Parameters

| | Parameter | Range | Average | CONSTANTS K(0) | K(1) | K(2) | K(3) | WAVELENGTHS 1 | 2 | 3 | R | R² | NIR STD ERROR |
|---|---|---|---|---|---|---|---|---|---|---|---|---|---|
| Simple Model | Exhaust Benzene | 3.928–8.758 | 6.028 | −2.988 | −22.506 | −46.304 | −14.849 | 2022 | 2180 | 2134 | 0.9345 | 0.8733 | 0.396 |
| | Total Toxics | 20.378–28.947 | 23.996 | 11.788 | 389.099 | 54.313 | −171.058 | 1138 | 1634 | 2134 | 0.8566 | 0.7338 | 1.030 |
| Complex Model Phase 1 | Exhaust Benzene | 11.621–34.341 | 22.047 | 245.214 | −3600.977 | 200.218 | −75.836 | 1584 | 1834 | 2134 | 0.9116 | 0.8310 | 2.190 |
| | Total Toxics | 26.926–55.943 | 40.762 | −72.494 | 1388.958 | 973.861 | −1154.131 | 1942 | 1460 | 1436 | 0.8464 | 0.7164 | 3.650 |
| | NOx | 541.621–787.850 | 667.901 | −71.367 | 3919.725 | −531.758 | −772.045 | 1594 | 1784 | 2166 | 0.9413 | 0.8860 | 20.600 |
| | Total VOC | 788.472–1367.134 | 1017.096 | −6476.446 | 2144.611 | 6147.0174 | 18538.080 | 1652 | 1812 | 1854 | 0.6572 | 0.4319 | 90.100 |
| Complex Model Phase 2 | Exhaust Benzene | 24.038–69.104 | 45.153 | 129.761 | −898.464 | −180.853 | 500.829 | 1998 | 2180 | 1832 | 0.8833 | 0.7802 | 4.830 |
| | Total Toxics | 52.163–105.410 | 77.476 | 594.559 | 678.661 | −473.665 | −905.224 | 1184 | 1868 | 1620 | 0.8641 | 0.7467 | 6.190 |
| | NOx | 1105.700–1621.780 | 1363.990 | −135.187 | −1509.620 | −1099.619 | 8100.105 | 2166 | 1784 | 1594 | 0.9353 | 0.8748 | 45.100 |
| | Total VOC | 1085.869–1702.454 | 1294.537 | −1757.174 | 12823.980 | −6082.546 | −7165.477 | 1232 | 1876 | 2246 | 0.8467 | 0.7169 | 75.800 |

PLS Equations for EPA Parameters

| | Parameter | Range | Average | Wavelength Range (nm) | Factors | R | R² | NIR STD ERROR |
|---|---|---|---|---|---|---|---|---|
| Simple Model | Exhaust Benzene | 3.928–8.758 | 6.028 | 1422–1480 | 7 | 0.9494 | 0.9014 | 0.371 |
| | Total Toxics | 20.376–28.947 | 23.996 | 1152–1214, 1600–1670, 2100–2160 | 11 | 0.9521 | 0.9065 | 0.692 |
| Complex Model Phase 1 | Exhaust Benzene | 11.621–34.341 | 22.047 | 1156–1208, 1560–1670 | 13 | 0.9756 | 0.9518 | 1.523 |
| | Total Toxics | 26.926–55.943 | 40.762 | 1136–1154, 1410–1480, 1600–1670 | 11 | 0.9492 | 0.9010 | 2.654 |
| | NOx | 541.621–787.850 | 667.901 | 1132–1260, 1320–1430, 1550–1670, 1780–1860, 2000–220 | 3 | 0.9301 | 0.8651 | 22.450 |
| | Total VOC | 788.472–1367.134 | 1017.096 | 1132–1202, 1402–1486, 1590–1670, 1780–1860, 2000–223 | 9 | 0.9172 | 0.8413 | 52.314 |
| Complex Model Phase 2 | Exhaust Benzene | 24.038–69.104 | 45.153 | 1146–1256, 1604–1670 | 12 | 0.9813 | 0.9629 | 2.301 |
| | Total Toxics | 52.163–105.410 | 77.476 | 1132–1154, 1156–1214, 1502–1626 | 14 | 0.9838 | 0.9679 | 2.855 |
| | NOx | 1105.700–1621.780 | 1363.990 | 1132–1190, 1592–1670, 1780–1798, 2098–2174 | 3 | 0.9339 | 0.8722 | 45.611 |
| | Total VOC | 1085.869–1702.454 | 1294.537 | 1132–1152, 1156–1258, 1420–1432 | 8 | 0.8715 | 0.7595 | 75.2603 |

TABLE VIII

EPA Parameters of Winter Gasolines by Mid-IR

Multiple Linear Regression Equations For EPA Parameters

|  | Parameter | Range | Average | CONSTANTS |  |  |  | WAVENUMBERS (cm-1) |  |  | R | R² | Mid-IR STD ERROR |
|---|---|---|---|---|---|---|---|---|---|---|---|---|---|
|  |  |  |  | K(0) | K(1) | K(2) | K(3) | 1 | 2 | 3 |  |  |  |
| Simple Model | Exhaust Benzene | 3.928–8.758 | 6.028 | 4.949 | 89.993 | −95.988 | 13.519 | 1607.8 | 1407.2 | 678 | 0.9721 | 0.9450 | 0.22 |
|  | Total Toxics | 20.378–28.947 | 23.996 | 21.273 | −70.822 | −30.716 | −23.077 | 1005.9 | 693.5 | 1503.6 | 0.9605 | 0.9226 | 0.24 |
| Complex Model Phase 1 | Exhaust Benzene | 11.621–34.341 | 22.047 | 31.182 | −41.235 | −203.784 | −276.36 | 2981.2 | 1333.9 | 693.5 | 0.8781 | 0.7711 | 3.51 |
|  | Total Toxics | 26.926–55.943 | 40.762 | 41.431 | −274.998 | −35.574 | 237.653 | 693.5 | 2973.5 | 1387.9 | 0.8533 | 0.7281 | 4.21 |
|  | NOx | 541.621–787.850 | 667.901 | 672.685 | −1636.269 | 5917.339 | −3969.414 | 1580.8 | 1175.7 | 894.1 | 0.8895 | 0.7912 | 26.10 |
|  | Total VOC | 788.472–1367.134 | 1017.096 | 518.485 | −5023.323 | 5174.315 | −3317.536 | 824.6 | 940.4 | 751.3 | 0.8001 | 0.6416 | 52.90 |
| Complex Model Phase 2 | Exhaust Benzene | 24.038–69.104 | 45.153 | 50.899 | 721.028 | −409.136 | −627.652 | 2784.4 | 1403.3 | 693.5 | 0.8839 | 0.07816 | 6.86 |
|  | Total Toxics | 52.163–105.410 | 77.476 | 102.905 | 906.374 | −430.719 | −556.302 | 940.4 | 1399.4 | 693.5 | 0.8624 | 0.7437 | 8.18 |
|  | NOx | 1105.700–1621.780 | 1363.990 | 1559.712 | −6956.908 | 16169.63 | −3404.095 | 1569.2 | 932.6 | 1399.4 | 0.8863 | 0.7855 | 55.10 |
|  | Total VOC | 1085.869–1702.454 | 1294.537 | 1457.897 | −4403.561 | 5490.922 | 13700.91 | 793.8 | 2865.4 | 1561.5 | 0.8264 | 0.6829 | 95.90 |

PLS Equations for EPA Parameters

|  | Parameter | Range | Average | Wavenumber Range | Factors | R | R² | NIR STD ERROR |
|---|---|---|---|---|---|---|---|---|
| Simple Model | Exhaust Benzene | 3.928–8.758 | 6.028 | 3131.6–2803.7, 1584.6–666.4 | 12 | 0.9861 | 0.9724 | 0.16 |
|  | Total Toxics | 20.376–28.947 | 23.996 | 3131.6–2769, 1592.3–666.4 | 10 | 0.9793 | 0.9590 | 0.18 |
| Complex Model Phase 1 | Exhaust Benzene | 11.621–34.341 | 22.047 | 3136–2751, 1657–680 | 13 | 0.9571 | 0.9160 | 2.22 |
|  | Total Toxics | 26.926–55.943 | 40.762 | 1657–680 | 12 | 0.9284 | 0.8619 | 3.12 |
|  | NOx | 541.621–787.850 | 667.901 | 1607.8–666 | 12 | 0.946 | 0.8949 | 19.25 |
|  | Total VOC | 788.472–1367.134 | 1017.096 | 1646.3–666 | 10 | 0.8834 | 0.7804 | 42.60 |
| Complex Model Phase 2 | Exhaust Benzene | 24.038–69.104 | 45.153 | 1646.3–666 | 12 | 0.936 | 0.8761 | 5.36 |
|  | Total Toxics | 52.163–105.410 | 77.476 | 1646.3–666 | 12 | 0.9325 | 0.8696 | 6.06 |
|  | NOx | 1105.700–1621.780 | 1363.990 | 1646.3–666 | 12 | 0.9452 | 0.8934 | 40.32 |
|  | Total VOC | 1085.869–1702.454 | 1294.537 | 1646.3–666 | 10 | 0.8975 | 0.8055 | 77.33 |

TABLE IX

EPA Parameters of Summer Gasolines by Mid-IR

Multiple Linear Regression Equations For EPA Parameters

| | | | | | CONSTANTS | | | | WAVENUMBERS (cm-1) | | | | | Mid-IR | |
|---|---|---|---|---|---|---|---|---|---|---|---|---|---|---|---|
| | Parameter | Range | Average | K(0) | K(1) | K(2) | K(3) | k(4) | 1 | 2 | 3 | 4 | R | $R^2$ | STD ERROR |
| Simple Model | Exhaust Benzene | 3.928–8.758 | 6.028 | 4.008 | 170.851 | −176.626 | 13.859 | | 1592.3 | 1291.4 | 674.2 | | 0.9593 | 0.9203 | 0.32 |
| | Total Toxics | 20.378–28.947 | 23.996 | 32.512 | −273.19 | 235.043 | 50.701 | | 2896.3 | 2888.6 | 674.2 | | 0.9276 | 0.8604 | 0.98 |
| Complex Model Phase 1 | Exhaust Benzene | 11.621–34.341 | 22.047 | 11.822 | −461.329 | 129.73 | 306.254 | | 1148.7 | 836.2 | 681.9 | | 0.9101 | 0.8283 | 2.48 |
| | Total Toxics | 26.926–55.943 | 40.762 | 50.264 | −105.264 | −283.88 | −346.03 | | 1411 | 824.6 | 693.5 | | 0.9301 | 0.8651 | 2.80 |
| | NOx | 541.621–787.850 | 667.901 | 600.821 | −8326.528 | 6305.637 | 700.296 | | 1333.9 | 909.5 | 670.3 | | 0.9473 | 0.8974 | 19.90 |
| | Total VOC | 788.472–1367.134 | 1017.096 | 978.086 | 0.1635 | 0.364 | −17.8491 | −65.958 | 3104/1138 | 2992/1200 | 3108/972 | 106/850 | 0.8235 | 0.6782 | 79.60 |
| Complex Model Phase 2 | Exhaust Benzene | 24.038–69.104 | 45.153 | 22.023 | −796.332 | 365.58 | 248.801 | | 1144 | 817 | 678 | | 0.922 | 0.8501 | 4.50 |
| | Total Toxics | 52.163–105.410 | 77.476 | 53.544 | −1004.017 | 441.743 | 288.945 | | 1148 | 817 | 678 | | 0.9436 | 0.8904 | 4.47 |
| | NOx | 1105.700–1621.780 | 1363.990 | 1148.166 | −20629.91 | 14989.53 | 1772.027 | | 932 | 910 | 670 | | 0.9524 | 0.9071 | 39.50 |
| | Total VOC | 1085.869–1702.454 | 1294.537 | 892.769 | −2.998 | −786.624 | 24.234 | 0.132 | 1565/1052 | 1561/2869 | 994/1187 | 824/126 | 0.9342 | 0.8727 | 55.20 |

PLS Equations for EPA Parameters

| | | | | | | | | Mid-IR | |
|---|---|---|---|---|---|---|---|---|---|
| | Parameter | Range | Average | Wavenumber Range (cm-1) | | | Factors | R | $R^2$ | STD ERROR |
| Simple Model | Exhaust Benzene | 3.928–8.758 | 6.028 | 2776.7–2726.6, 1557.6–1472.7, 712.7–670.3 | | | 2 | 0.9529 | 0.9080 | 0.34 |
| | Total Toxics | 20.376–28.947 | 23.996 | 3127.8–3019.8, 1530.6–1399.4, 840.1–666.4 | | | 10 | 0.9403 | 0.8842 | 1.01 |
| Complex Model Phase 1 | Exhaust Benzene | 11.621–34.341 | 22.047 | 2900.2–2857.7, 1210.4–662.6 | | | 4 | 0.9100 | 0.8281 | 2.52 |
| | Total Toxics | 26.926–55.943 | 40.762 | 2826.9–2749.7, 720.5–670.3 | | | 8 | 0.9496 | 0.9017 | 2.61 |
| | NOx | 541.621–787.850 | 667.901 | 1430.3–1376.3, 1044.5–874.8 | | | 13 | 0.9879 | 0.9759 | 11.72 |
| | Total VOC | 788.472–1367.134 | 1017.096 | 3134–3058, 3008–2962, 1260–1108, 1012–934, 888–812 | | | 11 | 0.9107 | 0.8294 | 66.16 |
| Complex Model Phase 2 | Exhaust Benzene | 24.038–69.104 | 45.153 | 3085–2746, 1666–694 | | | 8 | 0.9299 | 0.8647 | 7.67 |
| | Total Toxics | 52.163–105.410 | 77.476 | 2900–2865, 820–666 | | | 3 | 0.9253 | 0.8562 | 5.12 |
| | NOx | 1105.700–1621.780 | 1363.990 | 2927–2880, 1014–921, 732–666 | | | 5 | 0.9265 | 0.8584 | 50.45 |
| | Total VOC | 1085.869–1702.454 | 1294.537 | 3058–2746, 1650–686 | | | 11 | 0.9400 | 0.8836 | 60.29 |

TABLE X

RAMAN EPA Parameters for Winter Gasolines

Multiple Linear Regression Equations For EPA Parameters

| | Parameter | Range | Average | CONSTANTS K(0) | K(1) | K(2) | K(3) | k(4) | WAVENUMBERS (cm-1) 1 | 2 | 3 | 4 | R | R² | Mid-IR STD ERROR |
|---|---|---|---|---|---|---|---|---|---|---|---|---|---|---|---|
| Simple Model | Exhaust Benzene | 3.928–8.758 | 6.028 | 4.008 | 170.851 | −176.626 | 13.859 | | 1592.3 | 1291.4 | 674.2 | | 0.9593 | 0.9203 | 0.32 |
| | Total Toxics | 20.378–28.947 | 23.996 | 32.512 | −273.19 | 235.043 | 50.701 | | 2896.3 | 2888.6 | 674.2 | | 0.9276 | 0.8604 | 0.98 |
| Complex Model Phase 1 | Exhaust Benzene | 11.621–34.341 | 22.047 | 11.822 | −461.329 | 129.73 | 306.254 | | 1148.7 | 836.2 | 681.9 | | 0.9101 | 0.8283 | 2.48 |
| | Total Toxics | 26.926–55.943 | 40.762 | 50.264 | −105.264 | −283.88 | −346.03 | | 1411 | 824.6 | 693.5 | | 0.9301 | 0.8651 | 2.80 |
| | NOx | 541.621–787.850 | 667.901 | 600.821 | −8326.528 | 6305.637 | 700.296 | | 1333.9 | 909.5 | 670.3 | | 0.9473 | 0.8974 | 19.90 |
| | Total VOC | 788.472–1367.134 | 1017.096 | 978.086 | 0.1635 | 0.364 | −17.8491 | −65.958 | 3104/1138 | 2992/1200 | 3108/972 | 106/850 | 0.8235 | 0.6782 | 79.60 |
| Complex Model Phase 2 | Exhaust Benzene | 24.038–69.104 | 45.153 | 22.023 | −796.332 | 365.58 | 248.801 | | 1144 | 817 | 678 | | 0.922 | 0.8501 | 4.50 |
| | Total Toxics | 52.163–105.410 | 77.476 | 53.544 | −1004.017 | 441.743 | 288.945 | | 1148 | 817 | 678 | | 0.9436 | 0.8904 | 4.47 |
| | NOx | 1105.700–1621.780 | 1363.990 | 1148.166 | −20629.91 | 14989.53 | 1772.027 | | 932 | 910 | 670 | | 0.9524 | 0.9071 | 39.50 |
| | Total VOC | 1085.869–1702.454 | 1294.537 | 892.769 | −2.998 | −786.624 | 24.234 | 0.132 | 1565/1052 | 1561/2869 | 994/1187 | 824/126 | 0.9342 | 0.8727 | 55.20 |

PLS Equations for EPA Parameters

| | Parameter | Range | Average | Wavenumber Range (cm-1) | Factors | R | R² | Mid-IR STD ERROR |
|---|---|---|---|---|---|---|---|---|
| Simple Model | Exhaust Benzene | 3.928–8.758 | 6.028 | 2776.7–2726.6, 1557.6–1472.7, 712.7–670.3 | 2 | 0.9529 | 0.9080 | 0.34 |
| | Total Toxics | 20.376–28.947 | 23.996 | 3127.8–3019.8, 1530.6–1399.4, 840.1–666.4 | 10 | 0.9403 | 0.8842 | 1.01 |
| Complex Model Phase 1 | Exhaust Benzene | 11.621–34.341 | 22.047 | 2900.2–2857.7, 1210.4–662.6 | 4 | 0.9100 | 0.8281 | 2.52 |
| | Total Toxics | 26.926–55.943 | 40.762 | 2826.9–2749.7, 720.5–670.3 | 8 | 0.9496 | 0.9017 | 2.61 |
| | NOx | 541.621–787.850 | 667.901 | 1430.3–1376.3, 1044.5–874.8 | 13 | 0.9879 | 0.9759 | 11.72 |
| | Total VOC | 788.472–1367.134 | 1017.096 | 3134–3058, 3008–2962, 1260–1108, 1012–934, 888–812 | 11 | 0.9107 | 0.8294 | 66.16 |
| Complex Model Phase 2 | Exhaust Benzene | 24.038–69.104 | 45.153 | 3085–2746, 1666–694 | 8 | 0.9299 | 0.8647 | 7.67 |
| | Total Toxics | 52.163–105.410 | 77.476 | 2900–2865, 820–666 | 3 | 0.9253 | 0.8562 | 5.12 |
| | NOx | 1105.700–1621.780 | 1363.990 | 2927–2880, 1014–921, 732–666 | 5 | 0.9265 | 0.8584 | 50.45 |
| | Total VOC | 1085.869–1702.454 | 1294.537 | 3058–2746, 1650–686 | 11 | 0.9400 | 0.8836 | 60.29 |

TABLE XI

RAMAN EPA Parameters for Summer Gasolines

Multiple Linear Regression Equations For EPA Parameters

| | Parameter | Range | Average | CONSTANTS K(0) | K(1) | K(2) | K(3) | WAVENUMBERS 1 | 2 | 3 | R | R² | RAMAN STD ERROR |
|---|---|---|---|---|---|---|---|---|---|---|---|---|---|
| Simple Model | Exhaust Benzene | 3.928–8.758 | 6.114 | 6.793 | 4.766 | -3.965 | 5.582 | 1615.5 | 1461.2 | 994.5 | 0.9434 | 0.8900 | 0.385 |
| | Total Toxics | 20.376–33.368 | 24.31 | 22.562 | -24.177 | 44.348 | -21.906 | 1160.3 | 990.6 | 820.9 | 0.9307 | 0.8662 | 0.947 |
| Complex Model Phase 1 | Exhaust Benzene | 11.621–38.159 | 22.352 | 26.763 | -198.038 | 38.479 | 319.842 | 412.1 | 1249.1 | 608.8 | 0.9374 | 0.8787 | 2.04 |
| | Total Toxics | 26.926–59.520 | 41.032 | 43.044 | -196.996 | 34.126 | 342.811 | 412.1 | 994.5 | 608.8 | 0.9525 | 0.9073 | 223 |
| | NOx | 541.621–750.732 | 661.5 | 752.811 | -93.884 | -613.241 | 809.095 | 2992.4 | 1165.6 | 1349.3 | 0.9655 | 0.9322 | 15.7 |
| | Total VOC | 788.472–1367.134 | 1016.812 | 919.275 | 12723.91 | -1002.92 | -4414.41 | 967.5 | 763.1 | 307.9 | 0.7650 | 0.5852 | 87.7 |
| Complex Model Phase 2 | Exhaust Benzene | 24.038–75.765 | 45.93 | 55.976 | 70.31 | 624.394 | -386.226 | 1249.1 | 608.8 | 412.1 | 0.9368 | 0.8776 | 3.93 |
| | Total Toxics | 52.163–109.781 | 77.992 | 85.748 | 59.826 | 605.97 | -361.684 | 994.5 | 604.9 | 412.1 | 0.9407 | 0.8849 | 4.37 |
| | NOx | 1105.700–1539.93 | 1363.99 | 1562.041 | -202.963 | 1689.016 | -1329.67 | 2992.4 | 1665.6 | 1349.3 | 0.9663 | 0.9337 | 32.3 |
| | Total VOC | 1085.869–1702.454 | 1299.398 | 1401.583 | -543.859 | 4059.328 | -2835 | 1380.2 | 554.8 | 331.1 | 0.8892 | 0.7907 | 68.9 |

PLS Equations for EPA Parameters

| | Parameter | Range | Average | Wavenumber Range (cm-1) | Factors | R | R² | RAMAN STD ERROR |
|---|---|---|---|---|---|---|---|---|
| Simple Model | Exhaust Benzene | 3.928–8.758 | 6.1114 | 1623.2–1607.8, 1468.9–1453.5, 1002.2–952.1 | 3 | 0.933 | 0.404 | |
| | Total Toxics | 20.376–33.368 | 24.31 | 1168.1–1141.1, 1033.1–911.4, 828.6–813.2 | 7 | 0.9583 | 0.768 | |
| Complex Model Phase 1 | Exhaust Benzene | 11.621–38.159 | 22.352 | 2965.4–2950, 1260.6–1237.5, 616.5–601.1, 439.1–400.5 | 7 | 0.9558 | 0.9136 | 1.832 |
| | Total Toxics | 26.926–59.520 | 41.032 | 1002.2–952.1, 635.8–570.2, 450.7–361.9 | 7 | 0.9733 | 0.9473 | 1.793 |
| | NOx | 541.621–750.732 | 661.5 | 3023.3–2953.8, 1684.9–1576.9, 1387.9–1310.8 | 4 | 0.9386 | 0.881 | 21.01 |
| | Total VOC | 788.472–1367.134 | 1016.812 | 1063.9–716.8, 346.5–61.1 | 12 | 0.9818 | 0.9639 | 30.061 |
| Complex Model Phase 2 | Exhaust Benzene | 24.038–75.765 | 45.93 | 1295.3–1210.5, 647.4–574.1, 450.7–365.8 | 10 | 0.9929 | 0.9859 | 1.522 |
| | Total Toxics | 52.163–109.781 | 77.992 | 1036.9–955.9, 666.6–547.1, 469.9–358.1 | 4 | 0.9178 | 0.8424 | 5.279 |
| | NOx | 1105.700–1539.93 | 1363.99 | 3031–2953.8, 1684.9–1607.8, 1387.9–1306.9 | 7 | 0.9706 | 0.9421 | 32.702 |
| | Total VOC | 1085.869–1702.454 | 1299.398 | 1418.8–1333.9, 593.4–516.2, 369.7–292.5 | 6 | 0.921 | 0.8482 | 60.8491 |

TABLE XII

Driveability Index of Gasolines by Near-IR, Mid-IR, and RAMAN Spectroscopies

Multiple Linear Regression Equations For Driveablity Index of Gasolines by NIR

| Gasoline Type | Range | Average | CONSTANTS | | | | WAVELENGTHS | | | R | $R^2$ | NIR Std. Error |
|---|---|---|---|---|---|---|---|---|---|---|---|---|
| | | | K(0) | K(1) | K(2) | K(3) | 1 | 2 | 3 | | | |
| Neat | 908.180–1472.040 | 1094.605 | 2380.663 | −3295.76 | −1368.48 | 3917.013 | 1234 | 1802 | 2060 | 0.9198 | 0.846 | 37.6 |
| MTBE | 881.665–1408.680 | 1048.106 | 1730.997 | −1864.35 | −7878.87 | 2750.927 | 1202 | 1234 | 2064 | 0.9069 | 0.8225 | 41.2 |

PLS Equations For Driveability Index of Gasolines by NIR

| Gasoline Type | Range | Average | Wavelength Range (nm) | Factors | R | $R^2$ | NIR Std. Error |
|---|---|---|---|---|---|---|---|
| Neat | 908.180–1472.040 | 1094.605 | 1132–1224, 1238–1264, 1594–1670, 2106–2164 | 11 | 0.9421 | 0.8876 | 33.21 |
| MTBE | 881.665–1408.680 | 1048.106 | 1170–1228, 1598–1670 | 10 | 0.9647 | 0.9306 | 27.18 |

Multiple Linear Regression Equations For Driveability Index of Gasolines by Mid-IR

| Gasoline Type | Range | Average | CONSTANTS | | | | WAVENUMBERS | | | R | $R^2$ | Mid-IR Std. Error |
|---|---|---|---|---|---|---|---|---|---|---|---|---|
| | | | K(0) | K(1) | K(2) | K(3) | 1 | 2 | 3 | | | |
| Neat | 908.180–1472.040 | 1094.605 | 898.48 | 7570.374 | 8622.292 | −7601.51 | 952 | 863.2 | 1187.3 | 0.8728 | 0.7618 | 47.1 |

PLS Equations For Driveability Index of Gasolines by Mid-IR

| Gasoline Type | Range | Average | Wavenumber Range (cm−1) | Factors | R | $R^2$ | NIR Std. Error |
|---|---|---|---|---|---|---|---|
| Neat | 908.180–1472.040 | 1094.605 | 3093–2726.6, 1781–720.5 | 5 | 0.8835 | 0.7806 | 45.62 |

Multiple Linear Regression Equations For Driveability Index of Gasolines by Raman

| Gasoline Type | Range | Average | CONSTANTS | | | | WAVENUMBERS | | | R | $R^2$ | Raman Std. Error |
|---|---|---|---|---|---|---|---|---|---|---|---|---|
| | | | K(0) | K(1) | K(2) | K(3) | 1 | 2 | 3 | | | |
| Neat | 908.180–1472.040 | 1094.605 | 954.872 | −911.393 | −1520.19 | 3705.512 | 1476.6 | 427.5 | 307.9 | 0.9274 | 0.8601 | 37.3 |
| MTBE | 881.665–1408.680 | 1048.106 | 1109.821 | −800.978 | −2561.6 | 2756.446 | 840.2 | 388.9 | 254 | 0.9053 | 0.8196 | 42 |

PLS Equations For Driveability Index of Gasolines by Raman

| Gasoline Type | Range | Average | Wavenumber Range (cm−1) | Factors | R | $R^2$ | Raman Std. Error |
|---|---|---|---|---|---|---|---|
| Neat | 908.180–1472.040 | 1094.605 | 3019.4–2710.8, 1681–207.7 | 8 | 0.9688 | 0.9386 | 25.78 |
| MTBE | 881.665–1408.680 | 1048.106 | 3019.4–2772.6, 1681–207.7 | 5 | 0.9179 | 0.8425 | 39.54 |

TABLE XIII

Estimated Errors in the Calculations Due to the Repeatabilities, Reproduceabilities, and/or EPA Tolerance Limit for the Primary Methods

| | METHOD | REPEATABILITY F(C) | REPRODUCIBILTY F(C) | EPA LIMITS | BASED UPON EPA TOLERANCE LIMITS | POSSIBLE ERRORS |
|---|---|---|---|---|---|---|
| DISTILLATIONS | | | | | | |
| IBP | ASTM D 3710 | 2(1) | 8(4) | | WINTER SIMPLE MODEL | |
| 10% | ASTM D 3710 | 2(1) | 6(3) | | EXHAUST BENZENE | 0.481 |
| | | | | | TOTAL TOXICS | 0.481 |
| 20% | ASTM D 3710 | 4(2) | 11(6) | | COMPLEX 1 | |
| 30% | ASTM D 3710 | 4(2) | 13(7) | | EXHAUST BENZENE | 4.875 |
| | | | | | TOTAL TOXICS | 4.171 |
| 50% | ASTM D 3710 | 4(2) | 13(7) | 5 | NOx | 22.285 |
| 70% | ASTM D 3710 | 4(2) | 13(7) | | COMPLEX 2 | |
| | | | | | EXHAUST BENZENE | 8.864 |
| 80% | ASTM D 3710 | 5(3) | 20(11) | | TOTAL TOXICS | 8.248 |
| | | | | | NOx | 49.645 |
| 90% | ASTM D 3710 | 7(4) | 27(15) | 5 | SUMMER | |
| END PT | ASTM D 3710 | N/A | N/A | | SIMPLE MODEL | |
| | | | | | EXHAUST BENZENE | 0.481 |
| 200F | ASTM D 3710 | 2.49 | | 2.5 | TOTAL TOXICS | 2.051 |
| 300F | ASTM D 3710 | 4.2 | | 3.5 | COMPLEX 1 | |
| | | | | | EXHAUST BENZENE | 3.066 |
| RVP | | 0.27 | | 0.3 | TOTAL TOXICS | 4.713 |
| | | | | | NOx | 21.314 |
| COMPOSITION | | | | | | |
| SULFUR | ASTM D 2622 | 0.0021 | 0.0064 | 0.0025 | COMPLEX 2 | |
| | | | | | EXHAUST BENZENE | 6.296 |
| AROMATICS | P.I.A.N.O. | | | 2.7 | TOTAL TOXICS | 7.108 |
| | | | | | NOx | 45.154 |
| OLEFINS | P.I.A.N.O. | | | 2.5 | | |
| BENZENE | P.I.A.N.O. | | | 0.21 | DRIVEABILITY INDEX | 27.5 |
| OXYGENATE | ASTM D 5599 mtbe | | 0.29 | 0.3 | | |
| | ALL | | 0.24 | | | |

DETAILED DESCRIPTION OF THE INVENTION

Referring to the columns in Table 6, EPA Parameters of Winter Gasolines by NIR, and Table VII, EPA Parameters of Summer Gasolines by NIR; "range" is shows the high and low value measured in a set of roughly 100 samples, "average" s is the mathematical average of the samples for the parameter being measured; k(0) is the offset constant not connected with any particular wavelength; k(1) is a constant which is multiplied by the absorbance at wavelength 1; k(2) is a constant which is multiplied by the absorbance at wavelength 2, etc.; R is the correlation coefficient; and $R^2$ is the coefficient of determination. Standard error is a measure of the accuracy of calibration (in milligrams per mile) for NIR (Tables VI and VII), for Mid-IR (Tables VIII and IX), and for Raman (Tables X and XI). Similarly, Table XII relates the analogous ranges, averages, constants, and wavelengths for "driveability index" of gasolines by all three methods: NIR, Mid-IR, and Raman.

Tables A–G summarize preferred, more preferred and most preferred parameters of the process, composition and the apparatus of the invention.

TABLE A

High Correlation NIR Spectral Regions for EPA Parameters of Winter Gasolines

| | Physical Property | Spectral Units | Preferred | More Preferred | Most Preferred |
|---|---|---|---|---|---|
| Simple Model | Exhaust Benzene | nm | 800–2500 | 1132–2300 | 1132–1156, 1156–1214 1260–1320, 1600–1670 2000–2100, 2100–2200 |
| | Total Toxics | nm | 800–2500 | 1132–2300 | 1156–1214, 1430–1510 1600–1670, 1900–1970 2100–2162 |
| Complex Model Phase I | Exhaust Benzene | nm | 800–2500 | 1132–2300 | 1132–1156, 1156–1214 1320–1430, 1430–1510 1600–1670, 1780–1880 1900–1970, 2100–2162 |
| | Total Toxics | nm | 800–2500 | 1132–2300 | 1132–1156, 1156–1214 1400–1480, 1480–1550 1600–1670, 1780–1860 2100–2162 |
| | NOx | nm | 800–2500 | 1132–2300 | 1156–1214, 1214–1230 1320–1430, 1480–1600 1600–1670, 1780–1860 2000–2050, 2100–2200 |
| | Total VOC | nm | 800–2500 | 1132–2300 | 1132–1156, 1156–1260 1320–1480, 1594–1670 2000–2162 |
| Complex Model Phase II | Exhaust Benzene | nm | 800–2500 | 1132–2300 | 1132–1156, 1156–1214 1260–1300, 1350–1520 1550–1670, 1890–1930, 1970–2040, 2100–2200 |
| | Total Toxics | nm | 800–2500 | 1132–2300 | 1156–1214, 1320–1430 1430–1520, 1600–1670 1780–1860, 1950–2020 2100–2200 |
| | NOx | nm | 800–2500 | 1132–2300 | 1156–1214, 1280–1320 1400–1450, 1570–1600 1600–1670, 1780–1860 2100–2162 |
| | Total VOC | nm | 800–2500 | 1132–2300 | 1132–1260, 1320–1480 1550–1670, 1780–1860 |

TABLE B

High Correlation NIR Spectral Regions for BPA Parameters of Summer Gasolines

| | Physical Property | Spectral Units | Preferred | More Preferred | Most Preferred |
|---|---|---|---|---|---|
| Simple Model | Exhaust Benzene | nm | 800–2500 | 1132–230 | 1132–1156, 1156–1214 1214–1230, 1230–1264 1264–1320, 1400–1500 1600–1670, 1780–1860 1950–2100, 2100–2200 |
| | Total Toxics | nm | 800–2500 | 1132–230 | 1132–1156, 1156–1214 1400–1480, 1600–1670 2100–2162 |
| Complex Model Phase I | Exhaust Benzene | nm | 800–2500 | 1132–230 | 1132–1156, 1156–1214 1430–1480, 1550–1600 1600–1670, 1780–1860 2000–2100, 2100–2200 |
| | Total Toxics | nm | 800–2500 | 1132–230 | 1132–1156, 1156–1214 1400–1480, 1600–1670 1900–1970, 2100–2200 |
| | NOx | nm | 800–2500 | 1132–230 | 1132–1156, 1156–1214 1214–1230, 1230–1260 1320–1430, 1550–1670 1780–1860, 2000–2200 |

TABLE B-continued

High Correlation NIR Spectral Regions for BPA Parameters of Summer Gasolines

|   | Physical Property | Spectral Units | Preferred | More Preferred | Most Preferred |
|---|---|---|---|---|---|
|   | Total VOC | nm | 800–2500 | 1132–230 | 1132–1214, 1320–1500 1590–1670, 1780–1900 2000–2200 |
| Complex | Exhaust | nm | 800–2500 | 1132–230 | 1132–1156, 1156–1214 |
| Model | Benzene |   |   |   | 1214–1230, 1230–1260 |
| Phase II |   |   |   |   | 1600–1670, 1780–1860 1970–2040, 2100–2200 |
|   | Total | nm | 800–2500 | 1132–230 | 1132–1154, 1156–1214 |
|   | Toxics |   |   |   | 1450–1600, 1600–1670 1780–1900, 2100–2162 |
|   | NOx | nm | 800–2500 | 1132–230 | 1132–1156, 1156–1214 1230–1260, 1550–1600 1600–1670, 1780–1860 2070–2200 |
|   | Total VOC | nm | 800–2500 | 1132–2300 | 1132–1156, 1156–1260 1320–1480, 1780–1900 2160–2300 |

TABLE C

High Correlation Mid-IR Spectral Regions for EPA Parameters of Winter Gasolines

|   | Physical Property | Spectral Units | Preferred | More Preferred | Most Preferred |
|---|---|---|---|---|---|
| Simple Model | Exhaust Benzene | cm-1 | 400–4000 | 600–1680 2700–3500 | 3154–2800, 1635–650 |
|   | Total Toxics | cm-1 | 400–4000 | 600–1680 2700–3500 | 3132–2769-1593–650 |
| Complex Model Phase I | Exhaust Benzene | cm-1 | 400–4000 | 600–1680 2700–3500 | 3136–2751, 1657–660 |
|   | Total Toxics | cm-1 | 400–4000 | 600–1680 2560–3500 | 3132–2560, 1657–660 |
|   | NOx | cm-1 | 400–4000 | 600–1680 2700–3500 | 3154–2745, 1690–660 |
|   | Total VOC | cm-1 | 400–4000 | 600–1680 2700–3500 | 3132–2734, 1674–666 |
| Complex Model Phase II | Exhaust Benzene | cm-1 | 400–4000 | 600–1680 2700–3500 | 3160–2720, 1647–666 |
|   | Total Toxics | cm-1 | 400–4000 | 600–1680 2700–3500 | 3140–2730, 1647–650 |
|   | NOx | cm-1 | 400–4000 | 600–1680 2700–3500 | 3132–2700, 1684–650 |
|   | Total VOC | cm-1 | 400–4000 | 600–1680 2700–3500 | 3132–2745, 1647–666 |

TABLE D

High Correlation Mid-IR Spectral Regions for EPA Parameters of Summer Gasolines

|   | Physical Property | Spectral Units | Preferred | More Preferred | Most Preferred |
|---|---|---|---|---|---|
| Simple Model | Exhaust Benzene | cm-1 | 400–4000 | 600–1680 2700–3500 | 2840–2416, 2416–2366 1616–1472, 1317–1272 |
|   | Total Toxics | cm-1 | 400–4000 | 600–1680 2700–3500 | 3132–2888, 2400–2300 1531–1370, 841–650 |
| Complex Model Phase I | Exhaust Benzene | cm-1 | 400–4000 | 600–1680 2700–3500 | 2901–2857, 1650–650 |
|   | Total Toxics | cm-1 | 400–4000 | 600–1680 2700–3500 | 3140–2749, 1634–608 |

TABLE D-continued

High Correlation Mid-IR Spectral Regions for EPA Parameters of Summer Gasolines

| | Physical Property | Spectral Units | Preferred | More Preferred | Most Preferred |
|---|---|---|---|---|---|
| | NOx | cm-1 | 400–4000 | 600–1680 2700–3500 | 3078–2749, 1696–650 |
| | Total VOC | cm-1 | 400–4000 | 600–1680 2700–3500 | 3134–2962, 1260–650 |
| Complex Model Phase II | Exhaust Benzene | cm-1 | 400–4000 | 600–1680 2700–3500 | 3166–2746, 1680–650 |
| | Total Toxics | cm-1 | 400–4000 | 600–1680 2700–3500 | 3082–2746, 1666–658 |
| | NOx | cm-1 | 400–4000 | 600–1680 2700–3500 | 2932–2746, 1520–1460 1314–1254, 1034–666 |
| | Total VOC | cm-1 | 400–4000 | 600–1680 2700–3500 | 3093–2746, 1650–608 |

TABLE E

High Correlation Raman Spectral Regions for EPA Parameters of Winter Gasolines

| | Physical Property | Spectral Units | Preferred | More Preferred | Most Preferred |
|---|---|---|---|---|---|
| Simple Model | Exhaust Benzene | cm-1 | 61–4000 | 61–1700 2700–3500 | 3093–2730, 1681–331 |
| | Total Toxics | cm-1 | 61–4000 | 61–1700 2700–3500 | 3093–2734, 1681–234 |
| Complex Model Phase I | Exhaust Benzene | cm-1 | 61–4000 | 61–1700 2700–3500 | 3093–2734, 1681–200 |
| | Total Toxics | cm-1 | 61–4000 | 61–1700 2700–3500 | 3093–2726, 1681–200 |
| | NOx | cm-1 | 61–4000 | 61–1700 2700–3500 | 3093–2734, 1666–200 |
| | Total VOC | cm-1 | 61–4000 | 61–1700 2700–3500 | 3085–2726, 1681–223 |
| Complex Model Phase II | Exhaust Benzene | cm-1 | 61–4000 | 61–1700 2700–3500 | 3093–2726, 1681–200 |
| | Total Toxics | cm-1 | 61–4000 | 61–1700 2700–3500 | 3097–2726, 1681–200 |
| | NOx | cm-1 | 61–4000 | 61–1700 2700–3500 | 3097–2718, 1666–200 |
| | Total VOC | cm-1 | 61–4000 | 61–1700 2700–3500 | 3082–2726, 1674–246 |

TABLE F

High Correlation Raman Spectral Regions for EPA Parameters of Summer Gasolines

| | Physical Property | Spectral Units | Preferred | More Preferred | Most Preferred |
|---|---|---|---|---|---|
| Simple Model | Exhaust Benzene | cm-1 | 61–4000 | 61–1700 2700–3500 | 1624–950 |
| | Total Toxics | cm-1 | 61–4000 | 61–1700 2700–3500 | 1169–820 |
| Complex Model Phase I | Exhaust Benzene | cm-1 | 61–4000 | 61–1700 2700–3500 | 1261–400, 2966–2950 |
| | Total Toxics | cm-1 | 61–4000 | 61–1700 2700–3500 | 1003–361 |
| | NOx | cm-1 | 61–4000 | 61–1700 2700–3500 | 3024–2953, 1685–1165 |
| | Total VOC | cm-1 | 61–4000 | 61–1700 2700–3500 | 1064–61 |
| Complex Model Phase II | Exhaust Benzene | cm-1 | 61–4000 | 61–1700 2700–3500 | 1296–365 |
| | Total Toxics | cm-1 | 61–4000 | 61–1700 2700–3500 | 1037–358 |
| | NOx | cm-1 | 61–4000 | 61–1700 2700–3500 | 3031–2953, 1685–1306 |
| | Total VOC | cm-1 | 61–4000 | 61–1700 2700–3500 | 1419–292 |

TABLE G

High Correlation NIR, Mid-IR, and Raman Spectral Regions of Driveability Index of Gasolines

| Spectroscopy | Physical Property | Spectral Units | Preferred | More Preferred | Most Preferred |
|---|---|---|---|---|---|
| NIR | Driveability Index | nm | 800–2500 | 1132–2300 | 1132–1230, 1230–1264 1594–1670, 1780–1860 1940–2100, 2100–2164 |
| Mid-IR | Driveability Index | cm-1 | 400–4000 | 600–1781 2700–3500 | 3093–2726, 1781–720 3500–3300 |
| Raman | Driveability Index | cm-1 | 61–4000 | 200–1700 2700–3500 | 3020–2710, 1681–207 3500–3300 |

DESCRIPTION OF THE PREFERRED EMBODIMENTS

EXAMPLE I

The Invention Measuring Summer and Winter Gasolines

The purpose of this project is to use near infrared, (NIR, near-IR), mid infrared (mid-IR), and Raman spectroscopies to determine distillation properties, EPA parameters, and the driveability index of finished gasoline by each of near infrared, mid infrared, and Raman spectroscopies. The near-IR spectra are collected using a NIRSystems on-line 5000. The mid-IR spectra are collected using a MIDAC FOx FT-IR. The Raman Spectra are collected using a Nicolet FT-Raman spectrophotometer.

The samples are submitted to gas chromatography for analysis by ASTM D-3710 for distillation parameters. The distillation points of interest are the initial boiling points, 10% recovery, 20% recovery, 30% recovery, 50% recovery, 70% recovery, 80% recovery, 90% recovery, and end point. The volume is distilled at 200° F. and 300° F. and are extrapolated values, using the nearest distillation percentage on each side of the temperature. The samples are divided up into two calibration sets designated neat and MTBE. The neat group includes all non-oxygenated samples, while the MTBE set includes gasolines containing methyl-tert-butyl ether. Multiple linear regression and partial least squares regression are performed on the calibration sets. The results for the neat and MTBE correlations by near-IR are listed in Tables I and II, respectively. The results for the neat correlations by mid-IR are listed in Table III. The results for the neat and MTBE correlations by Raman are listed in Tables IV and V, respectively.

For EPA gasoline exhaust parameters, there are three types of models. There is the "simple model", which came into use effective Jan. 1, 1995, the "complex model phase 1", which goes into effect in 1998, and the "complex model phase 2", which goes into effect in 2000. The samples are divided into two groups because any gasoline with a vapor pressure greater than 8.7 psi is considered winter gasoline, and lower than 8.7 psi is considered summer gasoline. For winter gasolines, the RVP value is set to the fixed value of 8.7 psi in the calculations. However, for summer gasolines, the actual RVP value is used in the calculations. The simple model parameters are calculated using the total aromatics concentration, the benzene concentration, the weight percent oxygen from MTBE, and the Reid vapor pressure. The complex models are calculated using the variables in the simple model, along with the sulfur concentration, the olefins concentration, and the volume percent distilled at 200° F. and 300° F. The results for the winter and summer correlations by near-IR are listed in Tables VI and VII, respectively. The results for the winter and summer correlations by mid-IR are listed in Tables VIII and IX, respectively. The results for the winter and summer correlations by Raman are listed in Tables X and XI, respectively.

With the simple model, the points of interest are the values for exhaust benzene and total toxics (exhaust benzene plus the other volatile organic carbons). With the complex model phase 1 and phase 2, the points of interest are the values for exhaust benzene, total toxics and NOx.

The driveability index is a value for measuring the expected performance during a vehicle cold-start or drive-away. The index is based upon the 10%, 50%, and 90% distillation points of the gasoline. Better performance is expected from those fuels with a lower driveability index value. The gasolines are divided into the same two groups as for the distillation properties. The results for near-IR, mid-IR, and Raman are listed in Table XII.

The repeatability and reproducibility of the primary methods and the EPA tolerance limits are listed in Table XIII. Based upon the EPA tolerance limits, possible errors are calculated by altering the variables used to calculate values of interest in selected samples, and then averaging the differences from the original calculated values. These are also listed in Table XIII.

EXAMPLE II

Invention Controlling a Fuel Blender

Figure 13:
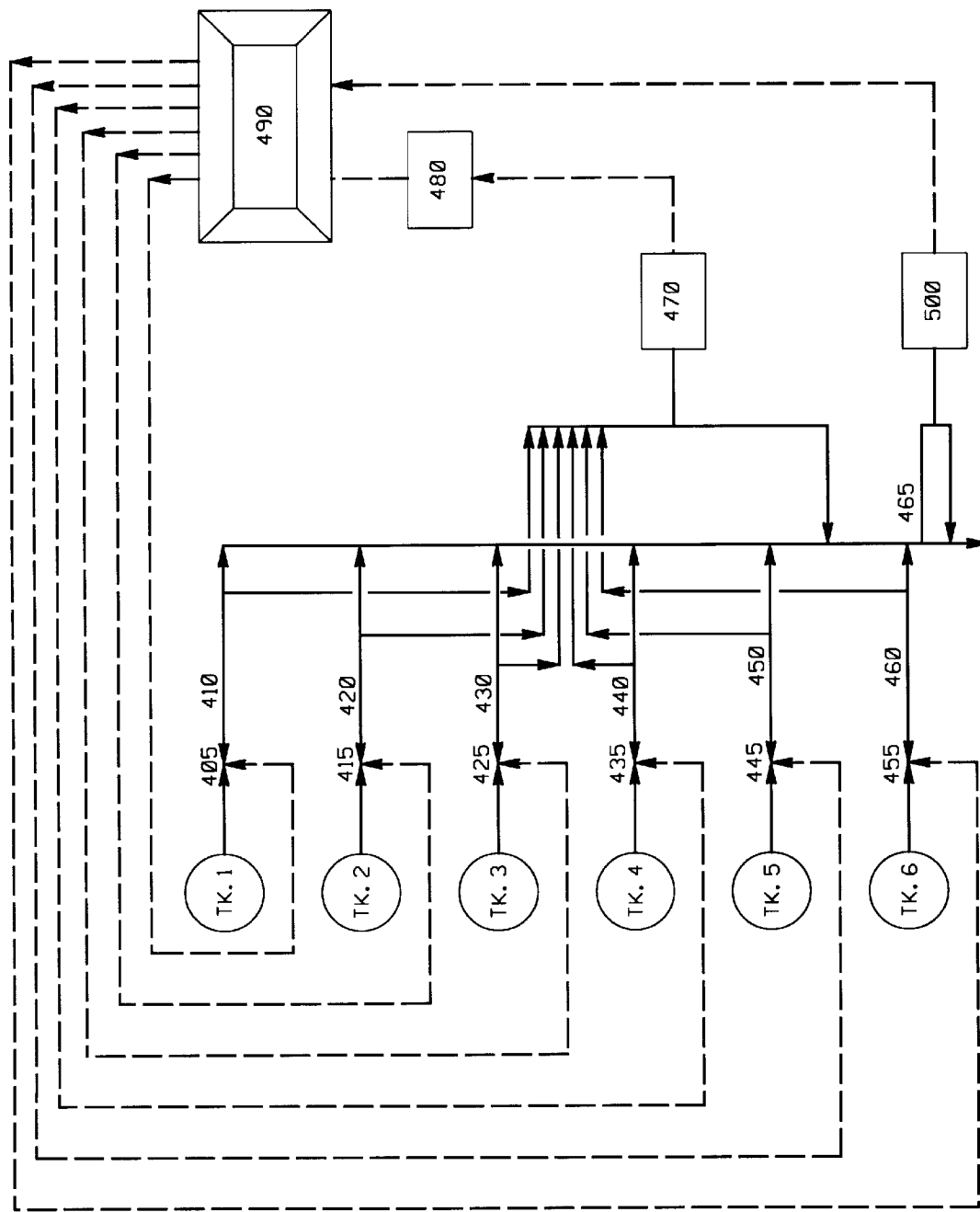
FIG. 13 illustrates schematically the fuel blending process described in Example II.

FIG. 13 represents a control scheme for an on-line blender in a refinery, with both feed-forward and feedback control loops, utilizing spectral analysis of EPA Fuel Emissions to provide control.

In FIG. 13, the use of multistreaming, whereby the component streams are switched sequentially to a single probe, using valves, is illustrated. However, multiplexing, whereby a probe is located in each component steam and finished gasoline line, or a combination of both, can also be used. In a multistreaming operation such as that illustrated in FIG. 1, component streams 410, 420, 430, 440, 450 and 460 are sequentially routed to the sample cell or sample in line probe of a spectrometer 470 which analyzes each stream for the EPA fuel emissions of interest, e.g., wt % oxygen. An output signal for each stream (proportional to wt % oxygen) is then transmitted to optimizing software such as GINO (Chevron Gasoline Inline Optimization). The GINO software, resident in blending computer 480, then continuously analyzes the signal, optimize and update the blend recipe in response thereto, and downloads the updated recipe to Blend Ratio Control (BRC) software which is resident in Distributed Control System (DCS) 490. The BRC software is capable of controlling DCS 490 which in turn may adjust the position of valves 405, 415, 425, 435, 445, and 455 to change the flow rates of component streams 410, 420, 430, 440, 450 and 460, respectively.

Another spectrometer 500 can also be used in a feedback mode. That is, a slip stream 465 of the finished blend is directed to the sample probe or sample cell of Raman spectrometer 500, which analyzes the finished blend for EPA fuel property compliance and other properties of interest. DCS 490 then receives the feedback signal from spectrometer 500 in the same manner as it receives the feed-forward signals from spectrometer 470. The DCS 490 is configured to allow direct control of valves 405, 415, 425, 435, 445 and 455 by the feedback control loop to override the recipe established by the feed-forward control loop when necessary.

Spectrometer 500 may be the same instrument as spectrometer 470, with feed-forward and feedback functions operating in a multiplexing or multistreaming mode.

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein. For example, while the invention has been illustrated with various gasolines, the invention is applicable to diesel fuel. Again, the examples use a simple NIR spectrometer whereas a Fourier Transform near infrared spectrometer, or an FT NIR, or other spectrometer may be substituted.

Reference to documents made in the specification is intended to result in such patents or literature being expressly incorporated herein by reference including any patents or other literature references cited within such documents.

What is claimed is:

1. A process for the prediction of an environmental pollution regulatory parameter for a liquid hydrocarbon fuel, due to evaporation and combustion in an internal combustion engine, comprising
    a) measuring the absorbance or Raman intensity of the fuel, or of at least one component of the fuel, with a spectrometer in at least one band of the electromagnetic spectrum;
    b) transforming the absorbance or Raman intensity measured in step a) by mathematical transformation comprising multivariant regression analysis to obtain a mathematically transformed absorbance or Raman intensity value;
    c) substituting said transformed absorbance or Raman intensity value into an equation or correlation which predicts said environmental pollution regulatory parameter, or one or more input values to a model for obtaining said environmental pollution regulatory parameter, of a liquid hydrocarbon fuel; and
    d) obtaining a prediction of said environmental pollution regulatory parameter or one or more of said input values of said liquid hydrocarbon fuel.

2. The process of claim 1 in which the environmental pollution regulatory parameter is selected from total toxics, exhaust benzene, volatile organic carbon, nitrogen oxides, and Reid vapor pressure.

3. The process of claim 1 in which the mathematical transformation includes use of a derivative.

4. The process of claim 1 in which the mathematical transformation comprises multiple linear regression, partial least squares, principal component regression, or level 3 or level 4 SIMCA and/or neural network.

5. The process of claim 4 in which the absorbance is measured and is accomplished in the near-infrared range or the mid-infrared range, and the fuel is gasoline.

6. The process of claim 5 in which the environmental pollution regulatory parameter is selected from total toxics, exhaust benzene, volatile organic carbon, nitrogen oxides, and Reid vapor pressure.

7. The process of claim 1 in which the absorbance is measured and is accomplished in the near-infrared range or the mid-infrared range, and the fuel is gasoline.

8. The process of claim 1 in which the Raman intensity is measured and the measuring of the Raman intensity is accomplished by a Raman Spectrometer, and the fuel is gasoline.

9. A process for controlling a fuel blending process to provide a liquid hydrocarbon fuel for an internal combustion engine in conformance with environmental pollution regulatory parameters comprising
    a) measuring the absorbance or Raman intensity of a fuel, or at least one component thereof, with a spectrometer in at least one band of the electromagnetic spectrum;
    b) transforming the absorbance or Raman intensity measured in step a) by mathematical transformation comprising multivariant regression analysis to obtain a mathematically transformed absorbance or Raman intensity value;
    c) substituting said transformed absorbance or Raman intensity value into an equation or correlation which predicts said environmental pollution regulatory parameters, or one or more input values to a model for obtaining said environmental pollution regulatory parameters, of a fuel, and obtaining a predicted environmental pollution regulatory parameter or one or more of said input values of the liquid hydrocarbon fuel; and
    d) utilizing the predicted environmental pollution regulatory parameter or one or more of said input values from step c) in controlling a fuel blending process.

10. The process of claim 9 in which the parameter is selected from total toxics, exhaust benzene; volatile organic carbon; nitrogen oxides, and Reid vapor pressure.

11. The process of claim 9 in which the mathematical transformation comprises use of a derivative.

12. The process of claim 9 in which the mathematical transformation comprises multiple linear regression, partial least squares, principal component regression, or level 3 or level 4 SIMCA and/or neural network.

13. The process of claim 12 in which the absorbance is measured and is accomplished in the near-infrared range or the mid-infrared range, and the fuel is gasoline.

14. The process of claim 13 in which the environmental pollution regulatory parameter is selected from total toxics, exhaust benzene, volatile organic carbon, nitrogen oxides, and Reid vapor pressure.

15. The process of claim 12 in which the absorbance is measured and is accomplished in the near-infrared range or the mid-infrared range, and the fuel is a diesel fuel.

16. The process of claim 9 in which the absorbance is measured and is accomplished in the near-infrared range or the mid-infrared range, and the fuel is gasoline.

17. The process of claim 9 in which the Raman intensity is measured and the measuring of the Raman intensity is accomplished by a Raman Spectrometer, and the fuel is gasoline.

18. A method for predicting emissions from evaporation and combustion of fuel in an internal combustion engine comprising
   a) taking multiple fuel samples and spectrally analyzing each of said samples to determine the concentration for at least one of benzene, total aromatics, weight percent oxygen, olefins, and sulfur;
   b) utilizing at least one concentration determined in step a) in a mathematical model or correlation for predicting total emissions from a concentration or concentrations determined in step a), and obtaining predicted emissions for each fuel sample;
   c) correlating spectral data obtained for each fuel sample with predicted emissions for each sample to obtain correlations between the spectral data and the predicted emissions;
   d) obtaining spectral data of additional fuel samples and predicting emissions for each of the additional fuel samples based on the correlations obtained in step c).

19. The method of claim 18 in which the fuel is gasoline, the fuel samples are spectrally analyzed using absorbance measurement, and absorbance measurement is accomplished in the near infrared range or the mid-infrared range.

20. A method for predicting emissions from evaporation and combustion of fuel in an internal combustion engine comprising
   a) taking multiple fuel samples and spectrally analyzing each of said samples to determine the Reid vapor pressure and/or distillation points thereof;
   b) utilizing at least one of the Reid vapor pressure and/or distillation points determined in step a) in a mathematical model or correlation for predicting total emissions from Reid vapor pressure and/or distillation points determined in step a), and obtaining predicted emissions for each fuel sample;
   c) correlating spectral data obtained for each fuel sample with predicted emissions for each sample to obtain correlations between the spectral data and the predicted emissions;
   d) obtaining spectral data of additional fuel samples and predicting emissions for each of the additional fuel samples based on the correlations obtained in step c).

21. The method of claim 20 in which the fuel is gasoline, the fuel samples are spectrally analyzed using absorbance measurement, and absorbance measurement is accomplished in the near infrared range or the mid-infrared range.

22. A method for controlling fuel blending for a fuel for an internal combustion engine comprising
   a) taking multiple fuel samples and spectrally analyzing each of said samples to determine the concentration for at least one of benzene, total aromatics, weight percent oxygen, olefins, and sulfur;
   b) utilizing at least one concentration determined in step a) in a mathematical model or correlation for predicting total emissions from a concentration or concentrations determined in step a), and obtaining predicted emissions for each fuel sample;
   c) correlating spectral data obtained for each fuel sample with predicted emissions for each sample to obtain correlations between the spectral data and the predicted emissions;
   d) obtaining spectral data for an additional fuel sample and predicting emissions for the additional fuel sample based on the correlations obtained in step c); and
   e) controlling a fuel blending process utilizing the correlations and predicting of emissions obtained in steps c) and d).

23. The method of claim 22 in which the fuel is gasoline, the fuel samples are spectrally analyzed using absorbance measurement, and absorbance measurement is accomplished in the near infrared range or the mid-infrared range.

24. The method of claim 22 in which the fuel is a diesel fuel, the fuel samples are spectrally analyzed using absorbance measurement, and absorbance measurement is accomplished in the near infrared range or the mid-infrared range.

25. A method for controlling fuel blending for a fuel for an internal combustion engine comprising
   a) taking multiple fuel samples and spectrally analyzing each of said samples to determine the Reid vapor pressure and/or distillation points thereof;
   b) utilizing at least one of the Reid vapor pressure and/or distillation points determined in step a) in a mathematical model or correlation for predicting total emissions from Reid vapor pressure and/or distillation points determined in step a), and obtaining predicted emissions for each fuel sample;
   c) correlating spectral data obtained for each fuel sample with predicted emissions for each sample to obtain correlations between the spectral data and the predicted emissions;
   d) obtaining spectral data for an additional fuel sample and predicting emissions for the additional fuel sample based on the correlations obtained in step c); and
   e) controlling a fuel blending process utilizing the correlations and predicting of emissions obtained in steps c) and d).

26. The method of claim 25 in which the fuel is gasoline, the fuel samples are spectrally analyzed using absorbance measurement, and absorbance measurement is accomplished in the near infrared range or the mid-infrared range.

27. A process for controlling a fuel blending process to provide a liquid hydrocarbon fuel for an internal combustion engine in conformance with environmental pollution regulatory parameters comprising
   a) measuring the absorbance or Raman intensity of a fuel, or at least one component thereof, with a spectrometer in at least one band of the electromagnetic spectrum;
   b) substituting said absorbance or Raman intensity into a correlation which predicts said environmental pollution regulatory parameter, or one or more input values to a correlation for obtaining said environmental pollution regulatory parameters, of a fuel, and obtaining a predicted environmental pollution regulatory parameter or one or more of said input values of the liquid hydrocarbon fuel; and
   c) utilizing the predicted environmental pollution regulatory parameter or one or more of said input values from step b) in controlling a fuel blending process.

28. The process of claim 27 in which the fuel is gasoline and the environmental pollution regulatory parameter is selected from total toxics, exhaust benzene, volatile organic carbon, nitrogen oxides, and Reid vapor pressure.

29. A process comprising
   a) measuring the absorbance or Raman intensity of a fuel, or at least one component of the fuel, with a spectrometer in at least one band of the electromagnetic spectrum;
   b) transforming the absorbance or Raman intensity measured in step a) by mathematical transformation comprising multivariant regression analysis to obtain a mathematically transformed absorbance or Raman intensity value;

c) substituting said transformed absorbance or Raman intensity value into a correlation which predicts said environmental pollution regulatory parameter, or one or more input values to a model for obtaining said environmental pollution regulatory parameter, of a liquid hydrocarbon fuel; and d) predicting emissions and/or one or more input values of the fuel upon substituting the transformed absorbance or Raman intensity value into said correlation, the correlation being the simple Environmental Protection Agency Model or a complex Environmental Protection Agency Model.

30. A process for determining environmental pollution regulatory parameters due to evaporation and combustion of a fuel for an internal combustion engine comprising a) measuring, with a spectrometer, at at least one band of the electromagnetic spectrum, the absorbance or Raman intensity of a calibration sample of a liquid hydrocarbon fuel, or component of the fuel;

b) performing mathematical transformation on the absorbance or Raman intensity measured, or a function thereof, of said calibration sample as individual independent variables in a model;

c) assigning and applying weighting constants, or their equivalents, to said independent variables;

d) calibrating a spectrometer utilizing known environmental pollution regulatory parameters and weighted individual independent variables produced from steps b) and c);

e) measuring, with the spectrometer calibrated, at at least one band of the electromagnetic spectrum, the absorbance or Raman intensity of a different liquid hydrocarbon fuel, or component thereof, of undetermined environmental pollution regulatory parameters;

f) performing mathematical transformation on the absorbance or Raman intensity measured, or a function thereof, as individual independent variables in a model, of said different liquid hydrocarbon fuel, or component thereof, of undetermined environmental pollution regulatory parameters;

g) applying the weighting constants, or equivalents thereof, to the individual independent variables obtained in step f) to determine one or more of the environmental pollution regulatory parameters of the different liquid hydrocarbon fuel.

31. The process of claim 30 in which the mathematical transformation includes use of a derivative and comprises multiple linear regression, partial least squares, principal component regression, or level 3 or level 4 SIMCA and/or neural network.

32. The process of claim 31 wherein the fuel is gasoline.

33. A process for control of environmental pollution regulatory parameters due to evaporation and combustion of a fuel for an internal combustion engine comprising a) measuring, with a spectrometer, at at least one band of the electromagnetic spectrum, the absorbance or Raman intensity of a calibration sample of a liquid hydrocarbon fuel, or component of the fuel;

b) performing mathematical transformation on the absorbance or Raman intensity measured, or a function thereof, of said calibration sample as individual independent variables in a model;

c) assigning and applying weighting constants, or their equivalents, to said independent variables;

d) calibrating a spectrometer utilizing known environmental pollution regulatory parameters and weighted individual independent variables produced from steps b) and c);

e) measuring, with the spectrometer calibrated, at at least one band of the electromagnetic spectrum, the absorbance or Raman intensity of a different liquid hydrocarbon fuel, or component thereof, of undetermined environmental pollution regulatory parameters;

f) performing mathematical transformation on the absorbance or Raman intensity measured, or a function thereof, as individual independent variables in a model, of said different liquid hydrocarbon fuel, or component thereof, of undetermined environmental pollution regulatory parameters;

g) applying the weighting constants, or equivalents thereof, to the individual independent variables obtained in step f) to determine one or more of the environmental pollution regulatory parameters of the different liquid hydrocarbon fuel; and h) controlling environmental pollution regulatory parameters, related to evaporation and combustion, of a fuel in response to values of the parameters determined in step g).

34. The process of claim 33 in which the mathematical transformation comprises multiple linear regression, partial least squares, principal component regression, or level 3 or level 4 SIMCA and/or neural network, the absorbance is measured, and the measuring is accomplished in the near-infrared range or the mid-infrared range.

35. The process of claim 34 in which the absorbance is measured and is accomplished in the near-infrared range or the mid-infrared range, and the fuel is gasoline.

36. The process of clam 34 in which the fuel is a diesel fuel.

37. The process of claim 33 in which the absorbance is measured and is accomplished in the near-infrared range or the mid-infrared range, and the fuel is gasoline.

38. A process for determining environmental pollution regulatory parameters due to evaporation and combustion of a fuel for an internal combustion engine comprising a) measuring, with a spectrometer, at at least one band of the electromagnetic spectrum, the absorbance or Raman intensity of a calibration sample of a liquid hydrocarbon fuel, or component of the fuel;

b) transforming the absorbance or Raman intensity measured in step a) by mathematical transformation comprising multivariant regression analysis to obtain a mathematically transformed absorbance or Raman intensity value;

c) substituting said transformed absorbance or Raman intensity value into an equation or correlation which predicts said environmental pollution regulatory parameter, or one or more input values to a model for obtaining said environmental pollution regulatory parameter, of a liquid hydrocarbon fuel, and obtaining a predicted environmental pollution regulatory parameter of the liquid hydrocarbon fuel;

d) calibrating a spectrometer utilizing known environmental pollution regulatory parameters and the environmental pollution regulatory parameter predicted in step c);

e) measuring, with the spectrometer calibrated, at at least one band of the electromagnetic spectrum, the absorbance or Raman intensity of a different liquid hydrocarbon fuel, or component thereof, of undetermined environmental pollution regulatory parameters;

f) transforming the absorbance or Raman intensity measured of said undetermined liquid hydrocarbon fuel by mathematical transformation comprising multivariant regression analysis to obtain a mathematically transformed absorbance or Raman intensity value;

g) substituting said transformed absorbance or Raman intensity value into an equation or correlation which predicts an environmental pollution regulatory parameter, or one or more input values to a model for obtaining an environmental pollution regulatory parameter, of a fuel, and obtaining a predicted environmental pollution regulatory parameter of said different liquid hydrocarbon fuel.

39. The process of claim 38 in which the mathematical transformation includes use of a derivative and comprises multiple linear regression, partial least squares, principal component regression, or level 3 or level 4 SIMCA and/or neural network.

40. The process of claim 39 in which the absorbance is measured and is accomplished in the near-infrared range or the mid-infrared range, and the fuel is gasoline.

41. The process of claim 38 in which the absorbance is measured and is accomplished in the near-infrared range or the mid-infrared range, and the fuel is gasoline.

42. The process of claim 38 in which the fuel is a diesel fuel.

43. A process for control of environmental pollution regulatory parameters due to evaporation and combustion of a fuel for an internal combustion engine comprising a) measuring, with a spectrometer, at at least one band of the electromagnetic spectrum, the absorbance or Raman intensity of a calibration sample of a liquid hydrocarbon fuel, or component of the fuel;

b) transforming the absorbance or Raman intensity measured in step a) by mathematical transformation comprising multivariant regression analysis to obtain a mathematically transformed absorbance or Raman intensity value;

c) substituting said transformed absorbance or Raman intensity value into an equation or correlation which predicts said environmental pollution regulatory parameter, or one or more input values to a model for obtaining said environmental pollution regulatory parameter, of a liquid hydrocarbon fuel, and obtaining a predicted environmental pollution regulatory parameter or one or more of said input values of the liquid hydrocarbon fuel;

d) calibrating a spectrometer utilizing known environmental pollution regulatory parameters and the environmental pollution regulatory parameter or one or more of said input values predicted in step c);

e) measuring, with the spectrometer calibrated, at at least one band of the electromagnetic spectrum, the absorbance or Raman intensity of a different liquid hydrocarbon fuel, or component thereof, of undetermined environmental pollution regulatory parameters;

f) transforming the absorbance or Raman intensity measured of said undetermined liquid hydrocarbon fuel by mathematical transformation comprising multivariant regression analysis to obtain a mathematically transformed absorbance or Raman intensity value;

g) substituting said transformed absorbance or Raman intensity value into an equation or correlation which predicts an environmental pollution regulatory parameter, or one or more input values to a model for obtaining an environmental pollution regulatory parameter, of a fuel, and obtaining a predicted environmental pollution regulatory parameter or one or more of said input values of said different liquid hydrocarbon fuel; and h) controlling environmental pollution regulatory parameters due to evaporation and combustion of a fuel in response to the environmental pollution regulatory parameter or one or more of said input values predicted in step g).

44. The process of claim 43 in which the mathematical transformation comprises multiple linear regression, partial least squares, principal component regression, or level 3 or level 4 SIMCA and/or neural network, the absorbance is measured, and the measuring is accomplished in the near-infrared range or the mid-infrared range.

45. The process of claim 44 in which the absorbance is measured and is accomplished in the near-infrared range or the mid-infrared range, and the fuel is gasoline.

46. The process of claim 43 in which the absorbance is measured and is accomplished in the near-infrared range or the mid-infrared range, and the fuel is gasoline.

* * * * *